(12) United States Patent
Kolbe et al.

(10) Patent No.: US 6,407,178 B1
(45) Date of Patent: Jun. 18, 2002

(54) CATIONIC POLYMERS, COMPLEXES ASSOCIATING SAID CATIONIC POLYMERS WITH THERAPEUTICALLY ACTIVE SUBSTANCES COMPRISING AT LEAST A NEGATIVE CHARGE, IN PARTICULAR NUCLEIC ACIDS, AND THEIR USE IN GENE THERAPY

(75) Inventors: Hanno V. J. Kolbe, Achenheim; Otmane Boussif, Strasbourg; Thierry Delair, Echalas; Laurent Veron, Lyon, all of (FR)

(73) Assignee: Transgene S.A., Strasbourg (FR)

( * ) Notice: Subject to any disclaimer, the term of this patent is extended or adjusted under 35 U.S.C. 154(b) by 0 days.

(21) Appl. No.: 09/463,249

(22) PCT Filed: Jul. 20, 1998

(86) PCT No.: PCT/FR98/01581

§ 371 (c)(1),
(2), (4) Date: Jan. 21, 2000

(87) PCT Pub. No.: WO99/05183

PCT Pub. Date: Feb. 4, 1999

(30) Foreign Application Priority Data

Jul. 21, 1997 (FR) .......................................... 97-09209
Dec. 12, 1997 (FR) .......................................... 97-15807

(51) Int. Cl.$^7$ ...................... A01N 43/04; A61K 31/74; A61K 39/245; C08F 116/00
(52) U.S. Cl. ............................. 525/328.2; 424/78.01; 424/78.08; 424/230; 435/172.3; 260/209
(58) Field of Search .................... 435/172.3; 424/78.01, 424/78.08; 514/44

(56) References Cited

U.S. PATENT DOCUMENTS

| 3,325,472 A | 6/1967 | Sackler ....................... 260/209 |
| 3,440,320 A | 4/1969 | Sackler ....................... 424/230 |
| 5,260,385 A | 11/1993 | Iio ........................... 525/328.2 |
| 5,629,184 A | * 5/1997 | Goldenberg et al. ..... 435/172.3 |

FOREIGN PATENT DOCUMENTS

| DE | 42 27 019 | 2/1994 |
| EP | 0 154 742 | 9/1985 |
| EP | 0 359 996 | 3/1990 |
| EP | 0 580 078 | 1/1994 |
| EP | 0 580 079 | 1/1994 |
| EP | 0 591 807 | 4/1994 |
| WO | 92 07023 | 4/1992 |
| WO | 95 03356 | 2/1995 |

* cited by examiner

Primary Examiner—Jeffrey Fredman
Assistant Examiner—Arum Kr. Chakrabarti
(74) Attorney, Agent, or Firm—Burns, Doane, Swecker & Mathis, L.L.P.

(57) ABSTRACT

The invention concerns novel cationic polymers of formula (I) in which n is a whole number between 0 and 5 and p is a whole number between 2 and 20,000, more particularly p ranges between 10 and 18,000, and advantageously between 200 and 1,000, characterized in that: at least 10%, advantageously 30 to 80%, preferably 70%, of the free $NH_2$ functions are substituted by identical or different hydrophilic R groups; said cationic polymer can further comprise at least a targeting element associated covalently or not with the free $NH_2$ functions and/or said hydrophilic R groups provided that said cationic: polymer contains at least 20%, preferably at least 30%, of free $NH_2$ functions. The invention also concerns a complex comprising at least said cationic polymer associated with at least a therapeutically active substance, in particular a nucleic acid comprising at least a negative charge. The invention is useful for transferring a nucleic acid into target cells, in particular for gene therapy.

33 Claims, 19 Drawing Sheets

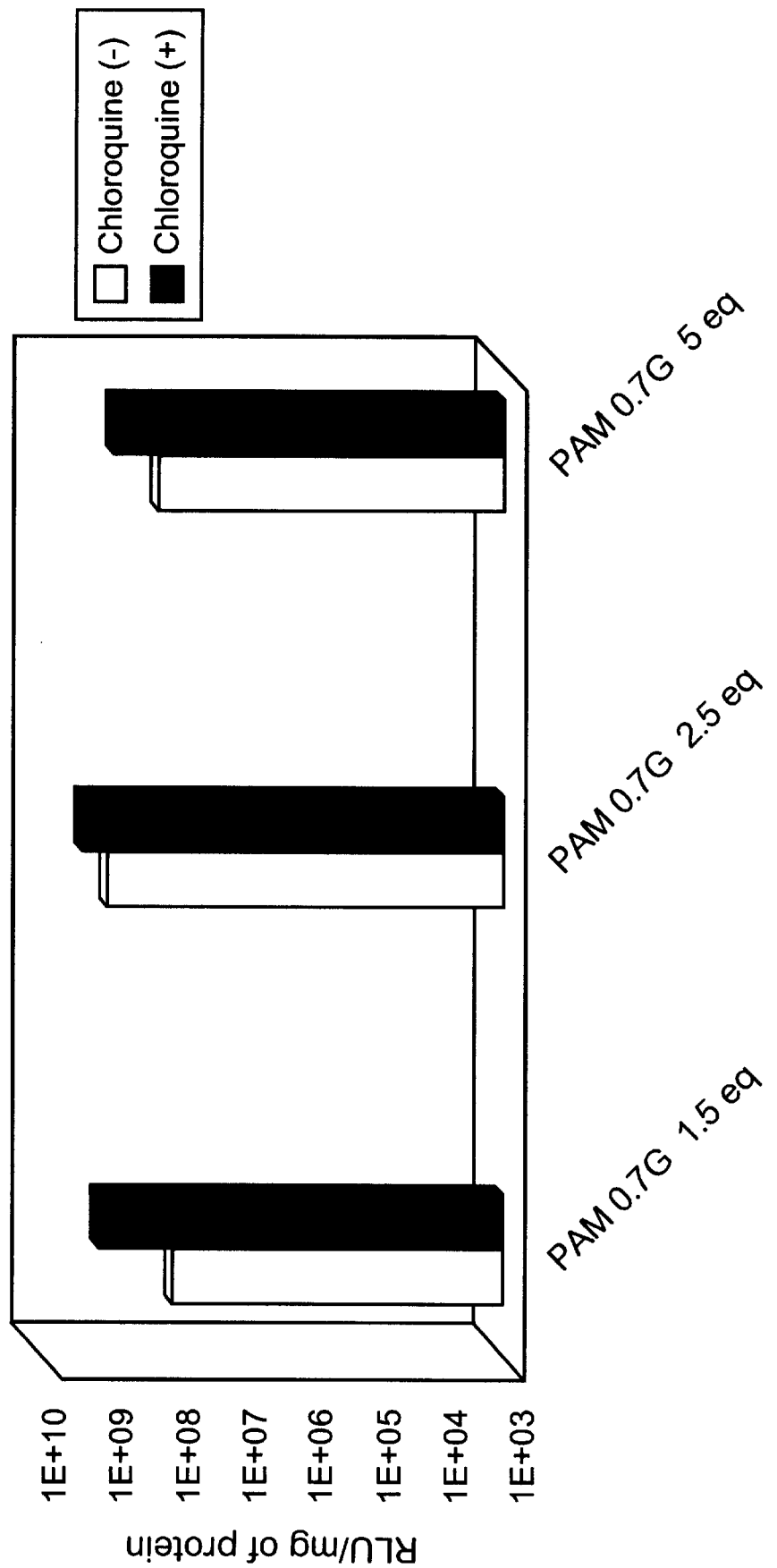

Figure 1:
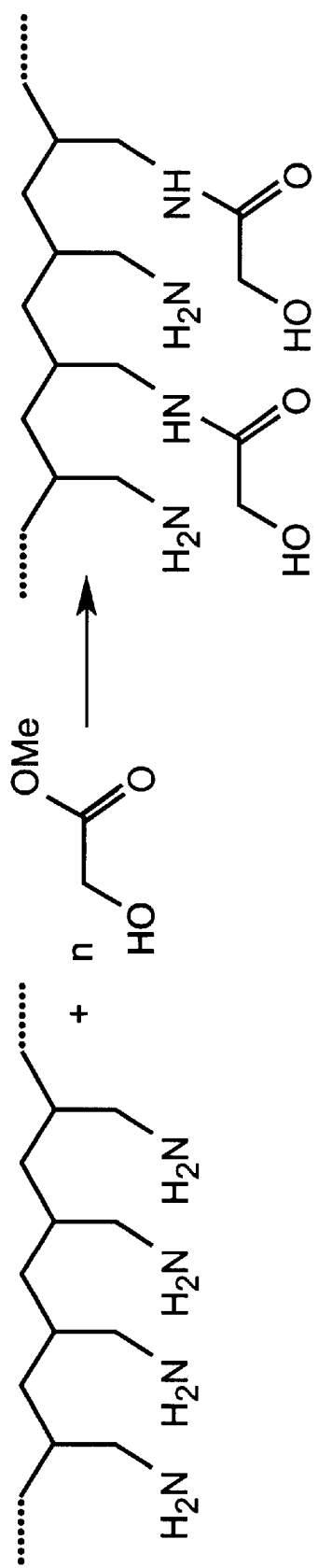

CATIONIC POLYMERS, COMPLEXES ASSOCIATING SAID CATIONIC POLYMERS WITH THERAPEUTICALLY ACTIVE SUBSTANCES COMPRISING AT LEAST A NEGATIVE CHARGE, IN PARTICULAR NUCLEIC ACIDS, AND THEIR USE IN GENE THERAPY

This application is a continuation of U.S. application Ser. No. 09/463,249, filed on Jan. 21, 2000, which was a national stage filing under 35 U.S.C. § 371 of International Application No. PCT/FR98/01581 filed on Jul. 20, 1998, which International Application was not published by the International Bureau in English on Feb. 4, 1999.

The present invention relates to novel cationic polymers which can be used for forming complexes of cationic polymers and of therapeutically active substances comprising at least one negative charge and the corresponding complexes, useful in particular for the transfer of a therapeutically active substance, in particular a nucleic acid, into a target cell.

Genetic diseases can be explained in particular by a dysfunction in the expression of specific genes or by the expression of mutated polypeptides which are nonfunctional in at least one cell type. The therapeutic solution which appears to be most appropriate for this type of condition is to transfer into specific target cells extracted and then reintroduced into the human body, or directly into the affected organs, the genetic information capable of correcting the defect observed. This may be for example the gene encoding the CFTR protein in the case of cystic fibrosis or the gene encoding dystrophin in the case of Duchenne's myopathy. In the context of this approach, also called gene therapy, the genetic information is introduced either in vitro into a cell extracted from the organ, the modified cell then being reintroduced into the body (ex vivo method), or directly in vivo into the appropriate tissue. Many publications also describe the use of a gene therapy protocol in order to obtain in the target cells the expression of a protein of therapeutic value by introducing the corresponding genetic information. The therapeutic value may for example lie in the possibility of eliminating a tumor, or failing this to slow down its progression, by transferring into the target cancer cells immunostimulatory genes (immunotherapy) which are capable of inducing or of activating a cell-mediated immune response toward the tumor, or the administration of genes encoding cytokines, of cytotoxic genes conferring toxicity on the cells expressing them, for example the tk gene of the Herpes Simplex virus type 1 (HSV-1), or of antioncogenes, such as for example the gene associated with retinoblastoma or p53, or of polynucleotides capable of inhibiting the activity of an oncogene, such as for example the antisense molecules or the ribozymes capable of degrading the messenger RNAs specific for the oncogenes.

During the past 30 years, several studies have described techniques relating to the transfer of this genetic information into cells, in particular mammalian cells. These different techniques may be divided into two categories. The first category relates to physical techniques such as microinjection, electroporation or particle bombardment which, although effective, are largely limited to applications in vitro and whose use is cumbersome and delicate. The second category involves techniques relating to molecular and cell biology for which the genetic material to be transferred is combined with a vector of a biological or synthetic nature which promotes the introduction of said material.

Currently, the most efficient vectors are viral, in particular adenoviral or retroviral, vectors. The techniques developed are based on the natural properties which these viruses possess for crossing the cell membranes, for escaping degradation of their genetic material and for causing their genome to penetrate into the cell nucleus. These viruses have already been the subject of many studies and some of them are already used experimentally as vectors for genes in humans for the purpose, for example, of a vaccination, an immunotherapy or a therapy intended to make up for a genetic deficiency. However, this viral approach has some limitations, in particular linked to the risks of dissemination in the host organism and in the environment of the infectious viral particles produced, to the risk of artefactual mutagenesis by insertion into the host cell in the case of retroviral vectors, and to the induction of immune and inflammatory responses in vivo during the therapeutic treatment. Accordingly, alternative, nonviral systems for transferring polynucleotides have also been developed.

There may be mentioned for example coprecipitation with calcium phosphate, the use of cationic lipids such as DOTMA: N-[1-(2,3-dioleyl-oxyl)propyl]-N,N,N-trimethylammonium (Felgner et al., 1987, PNAS, 84, 7413–7417), DOGS: dioctadecylamido-glycylspermine (Behr et al., 1989, PNAS, 86, 6982–6986 or Transfectam™), DMRIE: 1,2-dimiristyloxypropyl-3-dimethylhydroxyethylammonium and DORIE: 1,2-diooleyl-oxypropyl-3-dimethylhydroxyethylammonium (Felgner et al., 1993, Methods 5, 67–75), DC-CHOL: 3β-[N-(N',N'-dimethylaminoethane)carbamoyl]cholesterol (Gao and Huang, 1991, BBRC, 179, 280–285), DOTAP™ (McLachlan et al., 1995, Gene Therapy, 2, 674–622) or Lipofectamine™; or the use of polymers coupled to ligands recognized by a membrane receptor (for a review see Cotten and Wagner, 1993, Current Opinion in Biotechnology, 4, 705–710).

However, one of the major problems encountered when it is desired to transfer genes into target cells lies in the difficulty of causing the penetration of the nucleic acids because in particular of their polyanionic nature which prevents their passage across the cell membranes. The use of cationic polymers which can combine with the nucleic acids by electrostatic bonds makes it possible to solve this problem, at least partially. Thus, the document WO 95/24221 describes the use of dendritic polymers, document WO 96/02655 the use of polyethyleneimine, or of polypropyleneimine and the documents U.S. Pat. No. 5,595,897 and FR 2,719,316 the use of conjugates of polylysine.

The applicant company has now defined novel cationic polymers possessing particularly advantageous properties for the transfer into cells of therapeutically active substances comprising negative charges, in particular nucleic acids. Furthermore, these polymers have the advantage of being easily accessible, in particular by chemical synthesis, and inexpensive. They have a very low toxicity to cells, which constitutes a considerable advantage in the field of gene therapy.

The present invention relates first of all to a cationic polymer of formula I:

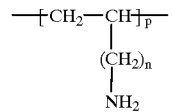

in which n is a whole number varying from 0 to 5 and p is a whole number varying from 2 to 20,000, more particularly p varies from 10 to 18,000 and advantageously from 200 to 1000, characterized in that:
at least 10%, advantageously from 30 to 80%, preferentially 70%, of the free $NH_2$ functions are substituted with identical or different hydrophilic R groups;

said cationic polymer may in addition comprise at least one targeting element combined covalently or not with the free $NH_2$ functions and/or with said hydrophilic R groups provided that said cationic polymer contains at least 20%, preferably at least 30%, of free $NH_2$ functions.

The invention relates more particularly to a cationic polymer defined by the following formula II:

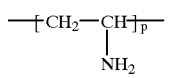

Advantageously, said cationic polymer is defined by the formula III:

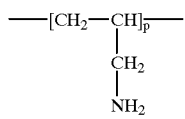

The polymers of formula II and III exhibit the characteristics as defined above for the polymer of more general formula I.

According to the present invention, "hydrophilic group" is understood to mean a group comprising at least one hydrophilic function. It may be for example a hydrophilic function chosen from the amine, hydroxyl, amide and ester functions.

These hydrophilic functions may be directly combined with the free $NH_2$ functions of the polymer through an N—C bond, or indirectly via an arm. In the latter case, the invention relates, for example, to a cationic polymer for which R is chosen from the groups:

R'—C=O, and;

—$(CH_2)n'$—R' where R' designates a group containing at least one hydrophilic function and n' is a whole number varying from 1 to 5.

According to an advantageous embodiment, the hydrophilic group R or R' consists of a polymer exhibiting hydrophilic properties, such as for example polyethylene glycol (PEG) or its derivatives, for example a methoxy-PEG, polyvinylpyrrolidone, poly-methyloxazoline, polyethyloxazoline, polyhydroxypropyl methacrylamide, polylactic acid, polyglycolic acid and cellulose derivatives such as hydroxymethylcellulose or hydroxyethylcellulose. According to the invention, the molecular weight of such polymers preferably varies from 300 to 5000, more particularly from 1000 to 4000, and is advantageously 2000. The preferred polymer for the use of such a variant of the invention is polyethylene glycol (PEG) and more particularly PEG 2000.

In general, when n and/or n' are greater than 5, the solubility of the cationic polymer thus formed or its capacity to form stable interactions with a negatively charged molecule may be disrupted. However, it is within the capability of persons skilled in the art to analyze the properties of such structures and to determine through experiments the most favorable conditions for the use of such polymers, in particular for the formation of complex with nucleic acids and for the transfection of cells.

Representative examples of cationic polymers according to the invention are glycolilated polyallylamines, in particular a polymer of formula III (n=1) where:

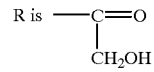

or alternatively the ethoxylated polyallylamines, in particular a polymer of formula IV (n=1) where R is —$(CH_2)_2$—OH and about 50 to about 80%, preferably from 50 to about 70%, of free $NH_2$ functions are substituted with R. According to an even more particular embodiment, p=592.

Advantageously, the invention relates to a cationic polymer as defined by formulae I, II, III or IV and which comprises, in addition, at least one targeting element. Such targeting elements can make it possible to direct the transfer of an active substance toward certain cell types or certain specific tissues (tumor cells, pulmonary epithelium cells, hematopoietic cell, muscle cell and the like). They can also make it possible to direct the transfer of an active substance toward certain preferred intracellular compartments such as the nucleus, the mitochondria and the like. They may be in addition elements which facilitate penetration into the cell or the lysis of the endosomes. Such targeting elements are widely described in the literature. They may be for example whole or part of lectins, peptides, in particular the peptide JTS-1 (see patent application WO 94/40958), oligonucleotides, lipids, hormones, vitamins, antigens, antibodies, ligands specific for membrane receptors, ligands capable of reacting with an antiligand, fusogenic peptides, nuclear localization peptides, or a combination of such compounds. In particular, they may be galactosyl residues which make it possible to target the receptor for the asialoglycoproteins at the surface of the hepatic cells, ligands which can react with receptors such as the receptors for growth factors, receptors for cytokines, lectins, or adhesion proteins; they may also be an antibody fragment such as the Fab fragment, a fusogenic peptide INF-7 derived from the influenza virus hemagglutinin HA-2 subunit (Plank et al., 1994, J. Biol. Chem. 269, 12918–12924), a nuclear localization signal derived from the SV40 virus T antigen or from the Epstein-Barr virus EBNA-1 protein.

This targeting element is attached covalently or noncovalently to the polymer of formula I, or II, or III, or IV. In the case where the cationic polymer is combined with an active substance comprising negative charges to form a complex according to the present invention, it is possible for said targeting element to be attached to said active substance.

Taken in isolation, the cationic polymer according to the invention contains monomers carrying free $NH_2$ functions which are capable of becoming $NH_3^+$ under appropriate pH conditions. Under these conditions, said cationic polymer is capable of forming a complex with at least one substance, in particular a therapeutically active substance, comprising negative charges.

The invention therefore also relates to a complex comprising at least one cationic polymer according to the present invention combined with at least one therapeutically active substance, comprising at least one negative charge.

Advantageously, such a complex is characterized in that said therapeutically active substance is chosen from nucleic acids and proteins.

"Nucleic acid" is understood to mean a synthetic or isolated natural, linear or circular, double-stranded or single-stranded, DNA and/or RNA fragment designating a precise succession of nucleotides, modified or otherwise, which make it possible to define a fragment or a region of a nucleic acid with no size limitation. According to a preferred embodiment, the therapeutically active substance is a nucleic acid chosen from the group consisting of a cDNA; a genomic DNA; a plasmid DNA; a messenger RNA; an antisense RNA; a ribozyme; a transfer RNA; a ribosomal RNA; or a DNA encoding such RNAs; a polynucleotide free of any compound facilitating its introduction into cells; a nucleic acid combined with at least one polypeptide, in particular a polypeptide of viral origin, and more particularly of adenoviral or retroviral origin, or a synthetic polypeptide; a nucleic acid combined with a ligand; a nucleic acid combined with amphiphilic agents, in particular cationic lipids; a nucleic acid combined with cationic polymers different from the polymers according to the present invention or with neutral or anionic polymers.

According to a variant of the invention, said therapeutically active substance contained in said complex is a nucleic acid which comprises a gene of interest and elements for expressing said gene of interest. Such a gene of interest may for example encode the whole or part of a ribozyme or of an antisense nucleic acid. According to another embodiment of the invention, said gene of interest encodes the whole or part of a polypeptide, in particular of a marker polypeptide (luciferase, β-galactosidase, product conferring resistance to an antibiotic, and the like) or of a polypeptide exhibiting a therapeutic or prophylactic activity (therapeutically active polypeptide), and more particularly an immunogenic activity of the cellular or humoral type. The term polypeptide extends with no restriction as to its size or its degree of glycosylation. It is also possible to mention, by way of examples of genes of interest, the genes encoding an enzyme, an enzyme inhibitor, a hormone, a cytokine, a membrane receptor, a structural polypeptide, a polypeptide forming a membrane channel, a transport polypeptide, an adhesion molecule, a ligand, a factor for regulating transcription, translation or replication, for stabilizing the transcripts, a coagulation factor, a polypeptide with antitumor effect, a polypeptide capable of slowing down the development of a bacterial, viral or parasitic infection, a toxin, or an antibody, such as for example the gene encoding the CFTR protein, dystrophin, factor VIII or IX, E6/E7 of HPV, MUC1, BRCA1, β-interferon, γ-interferon, interleukin (IL)2, IL-4, IL-6, IL-7, IL-12, tumor necrosis factor (TNF) type alpha, GM-CSF (Granulocyte Macrophage Colony Stimulating Factor), the Herpes Simplex virus type 1 (HSV-1) tk gene, the gene associated with restinoblastoma or p53 or the whole or part of immunoglobulins, such as the $F(ab)_2$, Fab', or Fab fragments or the anti-idiotypes (U.S. Pat. No. 4,699,880). Of course this list is not limiting, and the use of other genes may be envisaged.

In the case where the nucleic acid comprises the whole or part of a gene of interest encoding the whole or part of a polypeptide, it should be specified that said nucleic acid comprises, in addition, the elements necessary to ensure the expression of said DNA after transfer into a target cell, in particular promoter sequences and/or regulatory sequences which are efficient in said cell, and optionally the sequences required to allow the excretion or the expression, at the surface of the target cells, of said polypeptide. By way of example, there may be mentioned the promoters such as the promoters of the viruses RSV (Rous Sarcoma Virus), MPSV, SV40 (Simian Virus), CMV (Cytomegalovirus) or of the vaccinia virus, the promoters of the gene encoding muscle creatinine kinase, for actin, or for the pulmonary surfactant. It is in addition possible to choose a promoter sequence specific for a given cell type, or which can be activated under defined conditions. The literature provides a large amount of information relating to such promoter sequences. Moreover, said nucleic acid may comprise at least two identical or different sequences exhibiting a transcriptional promoter activity and/or at least two identical or different DNA coding sequences situated contiguously, distantly, in the same direction or in the opposite direction, relative to each other, provided that the function of the transcriptional promoter or the transcription of said sequences is not affected. Likewise, in this type of nucleic acid construct, it is possible to introduce "neutral" nucleic sequences or introns which do not hamper the transcription and are spliced before the translation step. Such sequences and their uses are described in the literature (WO 94/29471). Said nucleic acid may also contain sequences required for intracellular transport, for replication and/or for integration, for secretion, for transcription or translation. Such sequences are well known to persons skilled in the art. Moreover, the nucleic acids which can be used according to the present invention may also be nucleic acids modified such that it is not possible for them to become integrated into the genome of the target cell or nucleic acids stabilized with the aid of agents, such as for example spermine, which as they are do not have any effect on the transfection efficiency.

Advantageously, a specific ratio between the number of positive charges of said cationic polymer and the number of negative charges of said therapeutically active substance will be chosen. Without wishing to be limited by a specific ratio, quantities of the different charges will be preferably chosen such that the ratio between the positive charges of the cationic polymer and the negative charges of the active substance is between 1 and 30, in particular between 1.5 and 10, and preferably between 2.5 and 5. The calculation to arrive at such a ratio will take into consideration the negative charges carried by the active substance and the quantity of cationic polymer necessary to satisfy the ratio indicated above will be adjusted. When the polymer also contains one or more targeting elements, the quantities and the concentrations of targeting elements are adjusted as a function of their respective molar mass and of the number of their positive and/or negative charges.

The invention also relates to a method of preparing the cationic polymer/therapeutically active substance complexes according to the invention, characterized in that one or more polymers according to the invention are brought into contact with one or more therapeutically active substances comprising at least one negative charge and in that said complex is recovered. The recovery of said complex may be accompanied by a purification step. Several purification techniques may be envisaged, such as those based on the use of a density gradient or of a specific or nonspecific affinity column. These purification techniques are well known to persons skilled in the art who possess the necessary expertise for their use.

The invention also relates to a method for transferring a therapeutically active substance, in particular a nucleic acid, into a target cell in vitro, ex vivo or in vivo, characterized in that at least one complex according to the invention is brought into contact with target cells. According to one embodiment of the method according to the invention, cells cultured on an appropriate medium are brought into contact with a suspension comprising at least one cationic polymer/substance comprising negative charges complex as described in the present invention. After incubating for a certain period, the cells are washed and recovered. The transfection may be verified by any appropriate means, and in particular by measuring the expression of the gene carried by the nucleic acid forming a complex with the cationic polymer or by measuring the concentration of the polypeptide expressed. The method of transfection is well known per se and designates the introduction of a nucleic acid of interest into a cell for the purpose of expressing said nucleic acid.

"Target cells" according to the invention are understood to mean prokaryotic cells, yeast cells and eukaryotic cells, in particular animal cells, and in particular mammalian cells, especially human and/or cancer cells. In vivo, the complexes according to the invention may be administered into the interstitial or luminal space of tissues such as the lungs, the trachea, the skin, the muscle, the brain, the liver, the heart, the spleen, the bone marrow, the thymus, the bladder, the lymph, the blood, the pancreas, the stomach, the kidney, the ovaries, the testicles, the rectum, the peripheral or central nervous system, the eyes, the lymphoid organs, the cartilages and the endothelium.

The expression of a gene after transfection into cells may be analyzed by conventional techniques such as for example the detection of messenger RNAs by Northern blotting or digestion with S1 nuclease and/or the detection of proteins by Western blot immuno-precipitation or a functional test. The latter test is particularly suitable when the gene encodes a protein marker such as for example luciferase or β-galactosidase.

The invention also relates to the use of complexes as described above for the preparation of a medicament for the treatment of the human or animal body, in particular by gene therapy. According to a first possibility, the medicament may be administered directly in vivo or by an ex vivo approach which consists in removing the cells from the patient, in transfecting them in vitro according to the invention and in readministering them to said patient.

The invention relates to a pharmaceutical composition characterized in that it comprises at least one complex according to the present invention.

According to one variant of the invention, said pharmaceutical composition comprises at least one adjuvant capable of enhancing the capacity for transfection of said complex into a target cell in vitro, ex vivo or in vivo. More particularly, said adjuvant is chosen from the group consisting of a lysosomotropic agent such as for example chloroquine, a protic polar compound chosen in particular from propylene glycol, polyethylene glycol, glycerol, ethanol, 1-methyl-L-2-pyrrolidone or derivatives thereof, and an aprotic polar compound chosen in particular from dimethyl sulfoxide (DMSO), diethyl sulfoxide, di-n-propyl sulfoxide, dimethyl sulfone, sulfolane, dimethylformamide, dimethylacetamide, tetramethylurea, acetonitrile or derivatives thereof.

Depending on the mode of administration chosen, it is also possible to add to the composition of the invention a pharmaceutically acceptable carrier allowing administration to humans or to animals. The use of such carriers is described in the literature.

A complex or a pharmaceutical composition according to the invention may be administered in vivo in particular in a form which is injectable, in particular by the intramuscular route. It is also possible to envisage injection by the intratracheal, intranasal, epidermal, intravenous, intraarterial, intratumoral, intrapleural, or intracerebral route using a syringe or any other equivalent means. According to another embodiment, it is possible to use systems appropriate for the treatment of the airways or of the mucous membranes such as inhalation, instillation or aerosolization, by the topical route, by oral administration or any other means perfectly known to persons skilled in the art and applicable to the present invention. The administration may take place in a single dose or in a dose repeated once or several times after a certain time interval. The route of administration and the dosage which are most appropriate vary according to different parameters such as for example the individual or the disease to be treated, or alternatively the nucleic acid to be transfected or the target organ/tissue.

Finally, the invention relates to a cell transfected with a complex or a pharmaceutical composition as defined above, particularly a prokaryotic cell, a yeast or eukaryotic cell, in particular an animal cell, in particular a mammalian cell, and more particularly a cancer cell.

The present invention is illustrated by the following Examples 1 to 5, with reference to FIGS. 1 to 9.

LEGEND TO THE FIGURES

FIG. 1: It represents a diagram of the synthesis of the polyallylamines (PAM.) glycolilated at 50% (PAM/0.5G).

Figure 2:
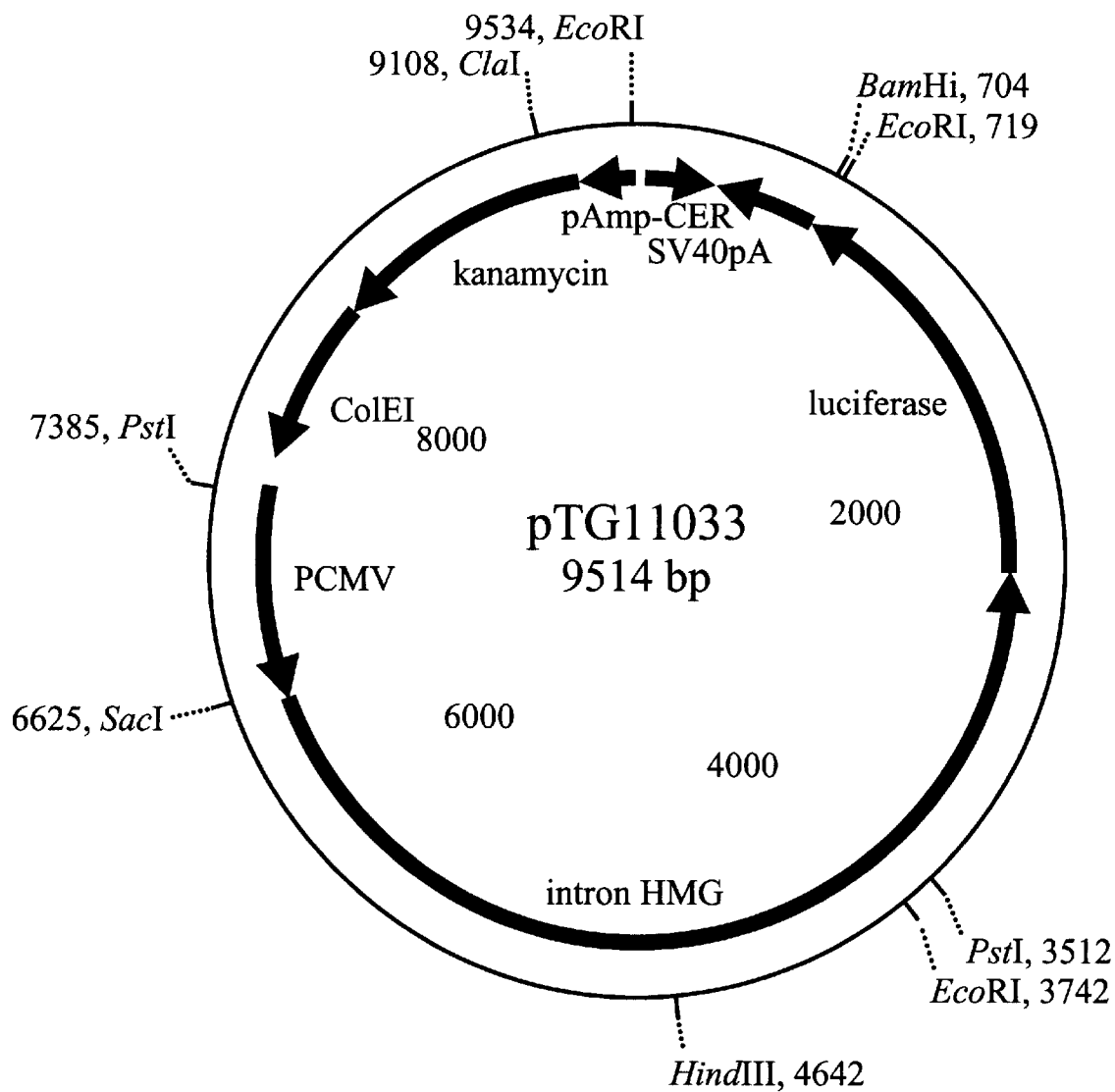

FIG. 2: map of the plasmid pTG11033.

Figure 3:
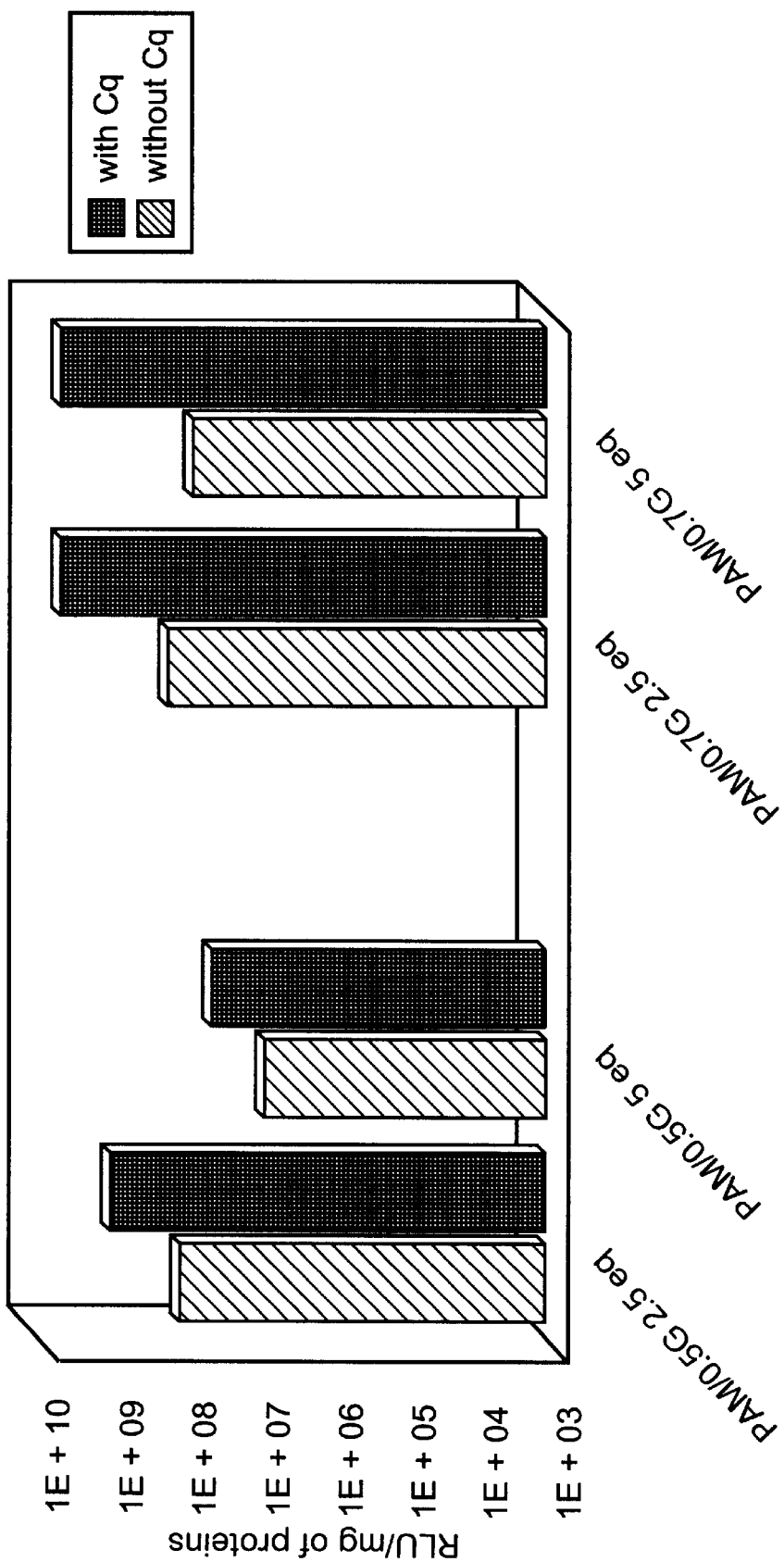

FIG. 3: Influence of the charge of the DNA/substituted cationic polymer complex on the transfection efficiency. The transfection efficiency is indicated by the quantity of luciferase produced (expressed as RLU/mg of protein). The "light" shaded columns represent the results observed in the absence of transfection adjuvant (chloroquine (Cq)), the "dark" shaded columns represent the results observed in the presence of 100 $\mu$M of chloroquine. PAM/0.5G: polymer polyallylamine glycolilated at 50%; PAM/0.7G: polymer polyallylamine glycolilated at 70%.

Figure 4:
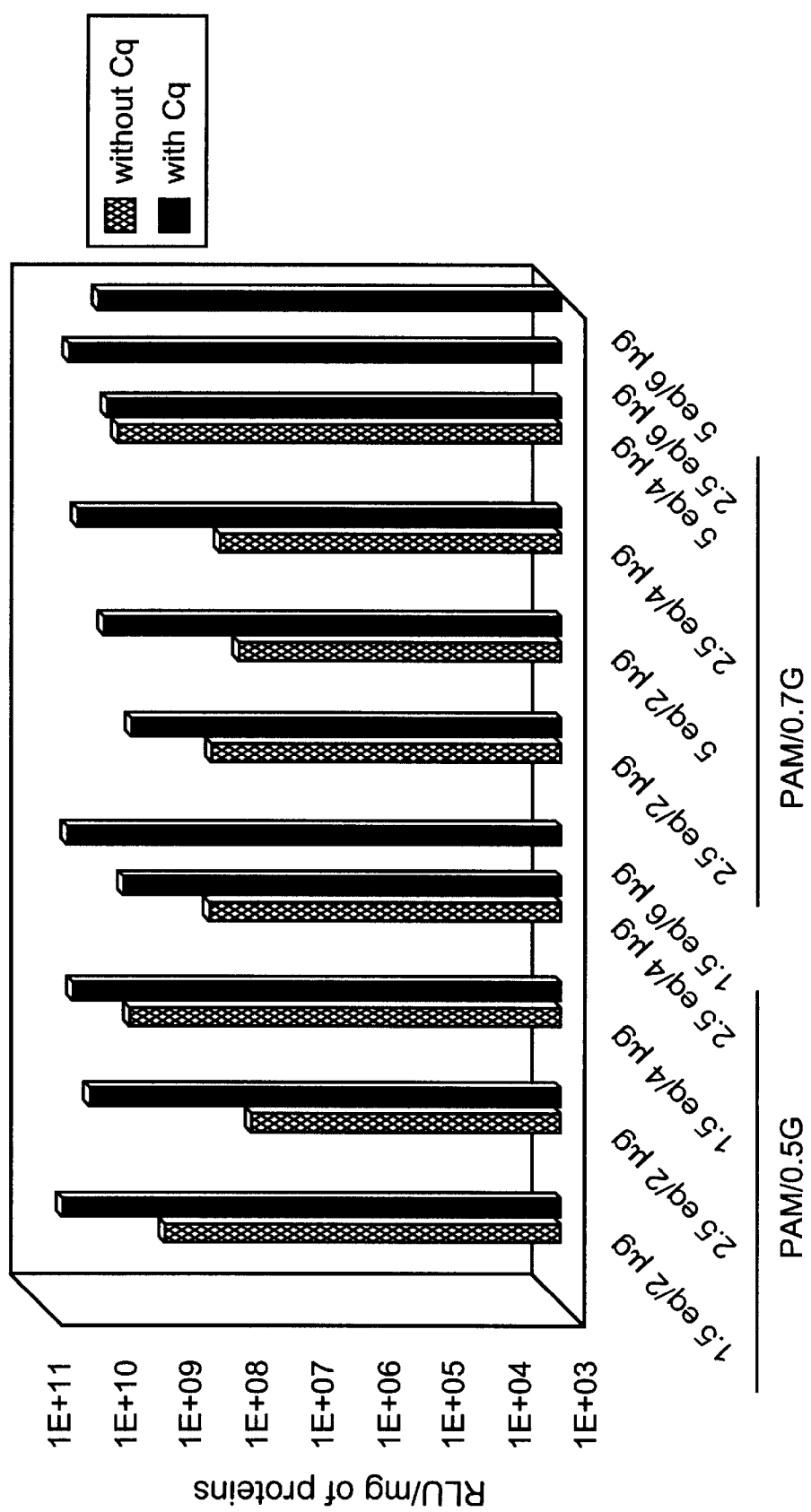

FIG. 4: Influence of the quantity of DNA on the transfection. The "light" shaded columns represent the results observed without chloroquine (Cq), the "dark" shaded columns represent the results observed in the presence of 100 $\mu$M of chloroquine.

Figure 5:
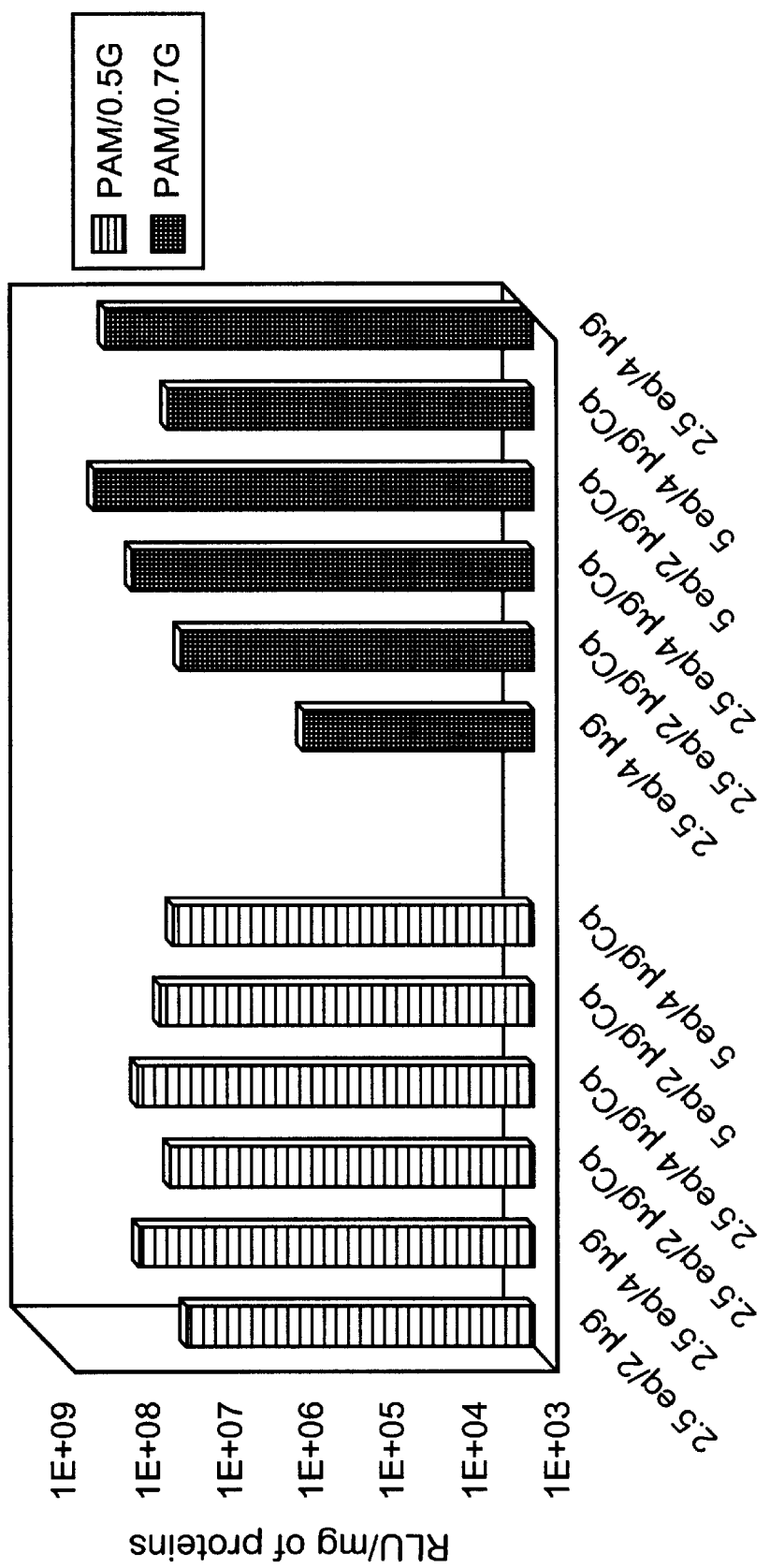

FIG. 5: Gene transfer into MRC5 cells. The light columns represent the results observed with PAM/0.5G, the dark columns represent the results observed with PAM/0.7G. The presence (Cq) or the absence of chloroquine is indicated on the x-axis.

Figure 6:
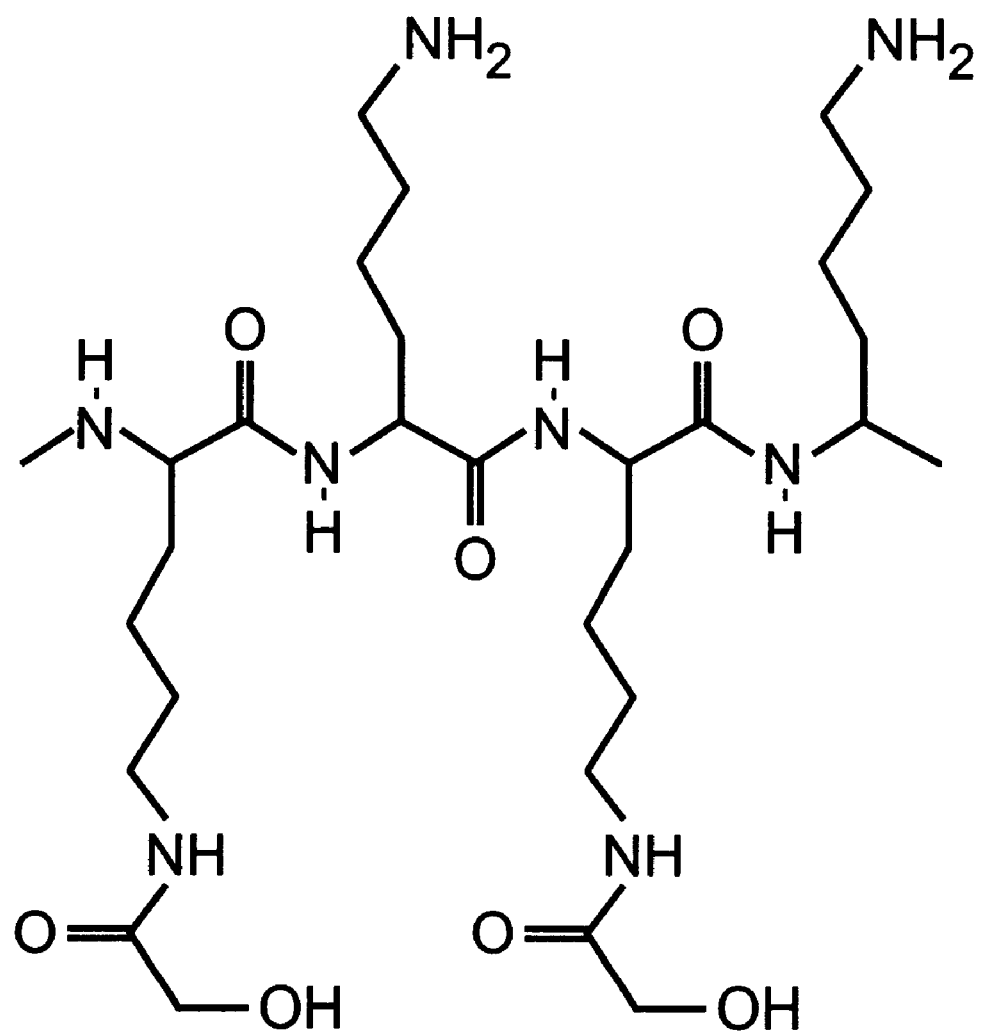

FIG. 6: Structure of PLL/0.7G (polylysine glycolilated at 70%).

Figure 7:
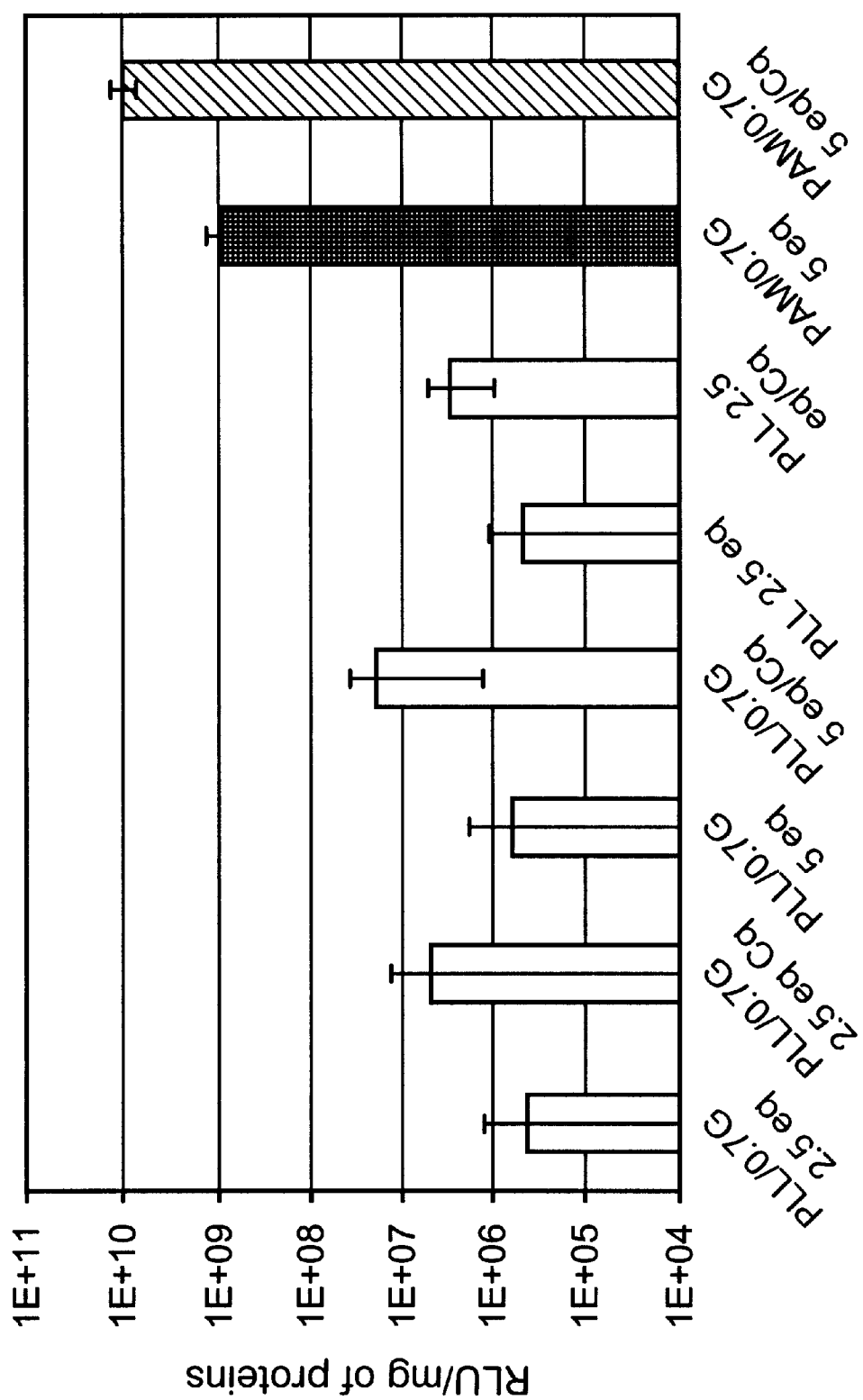

FIG. 7: Comparison of the transfection efficiencies for PAM/0.7G and PLL/0.7G. PLL: unsubstituted polylysine polymer; PLL/0.7G: polymer polylysine glycolilated at 70%.

Figure 8:
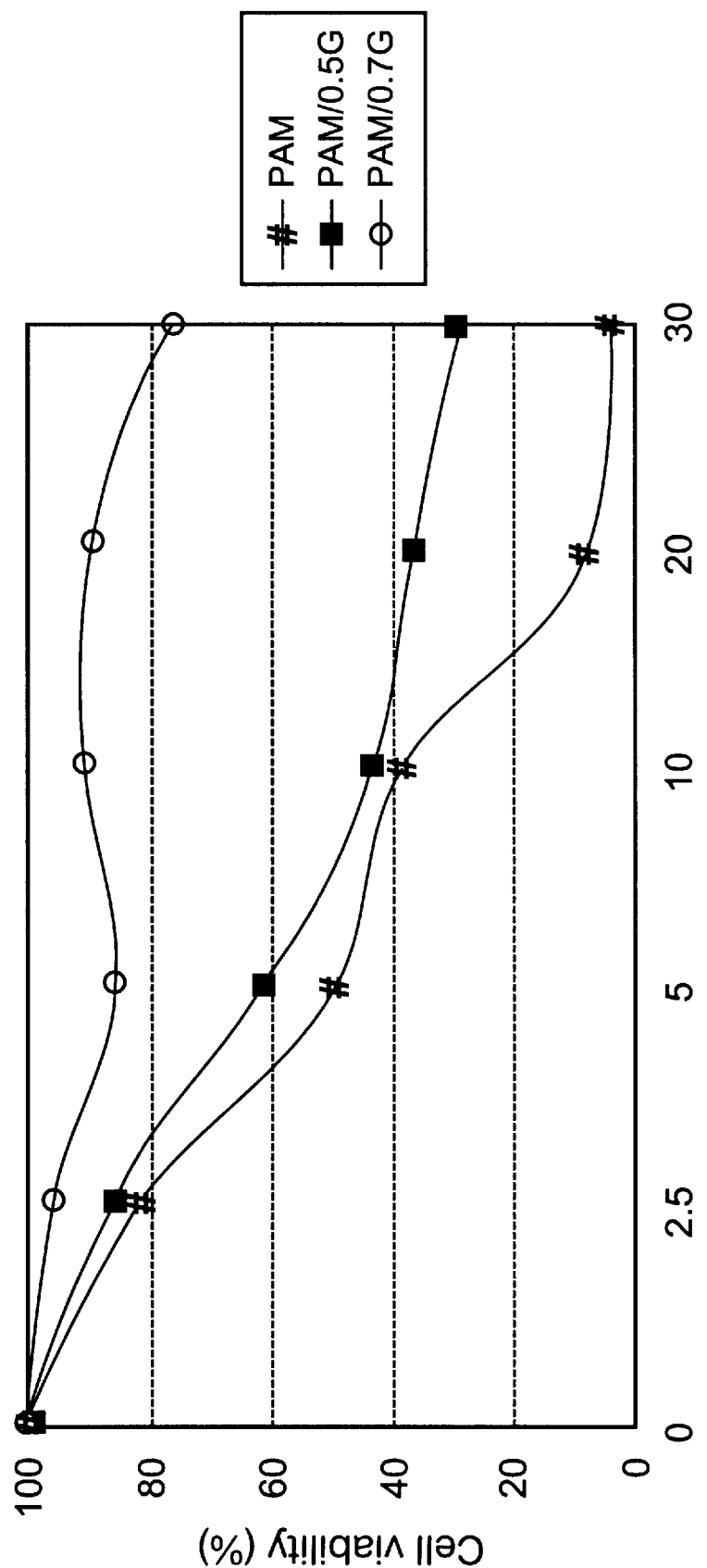

FIG. 8: Cytotoxicity of the substituted cationic polymers PAM/0.5G and PAM/0.7G.

Figure 9:
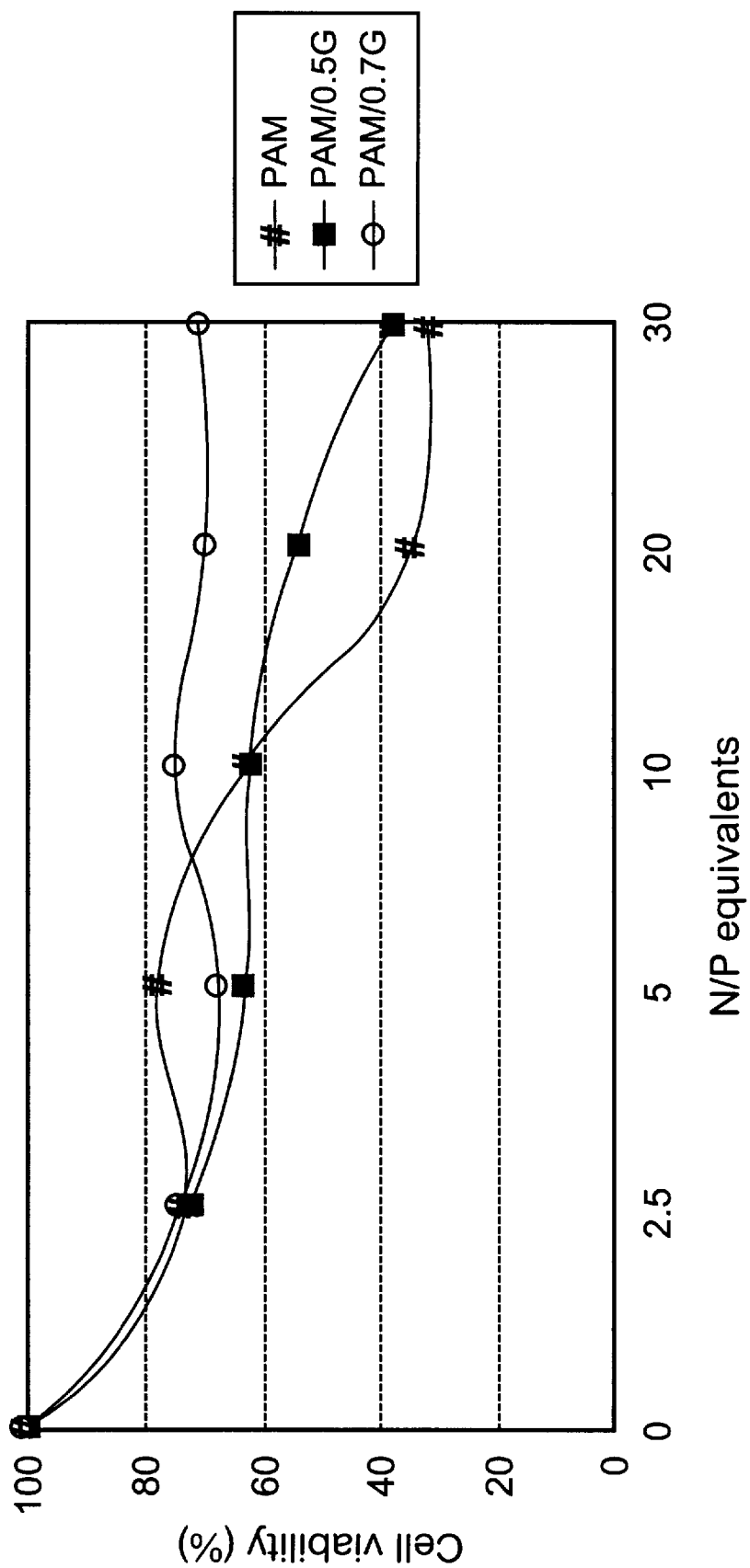

FIG. 9: Cytotoxicity of the plasmid DNA/substituted cationic polymer complexes (PAM/0.5G or PAM/0.7G).

Figure 10:
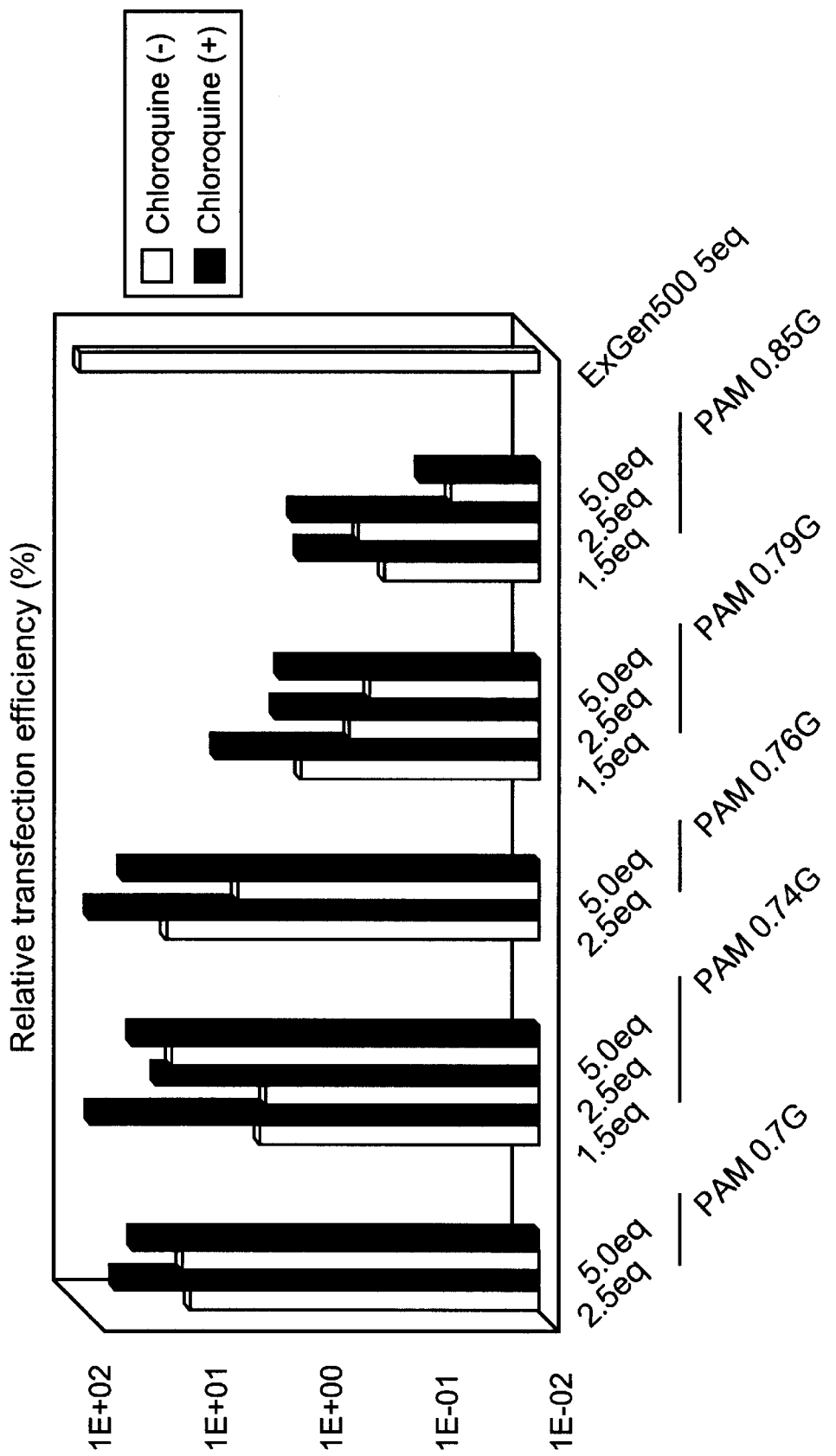
Figure 11A:
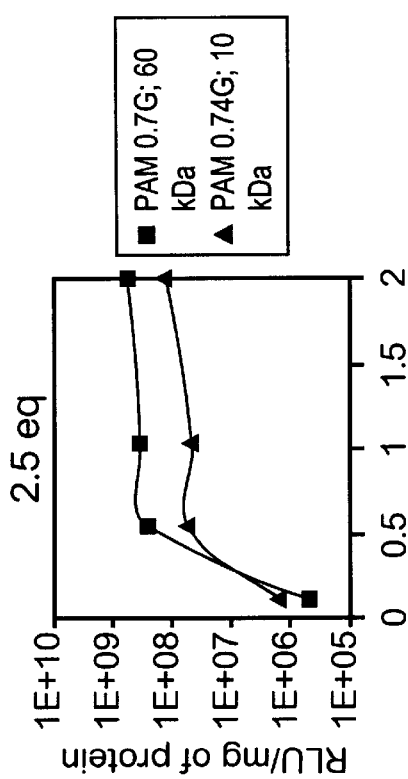
Figure 11C:
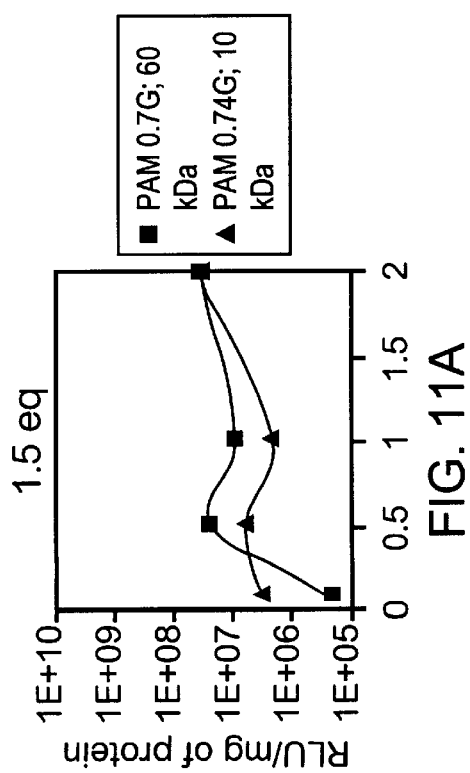
Figure 11B:
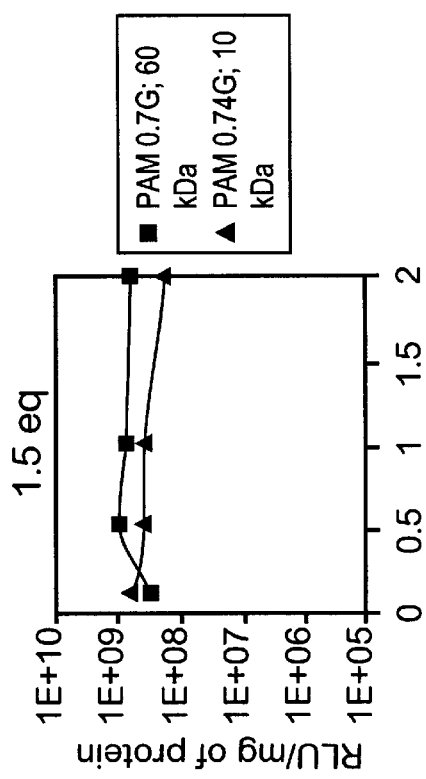
Figure 11D:
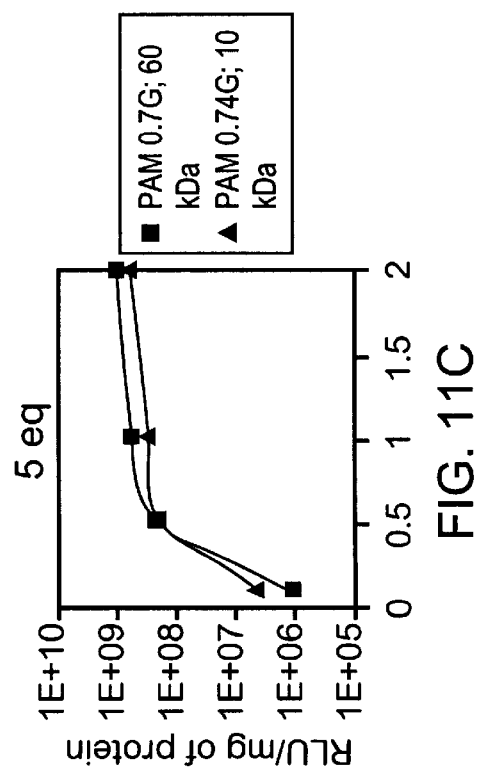
Figure 11F:
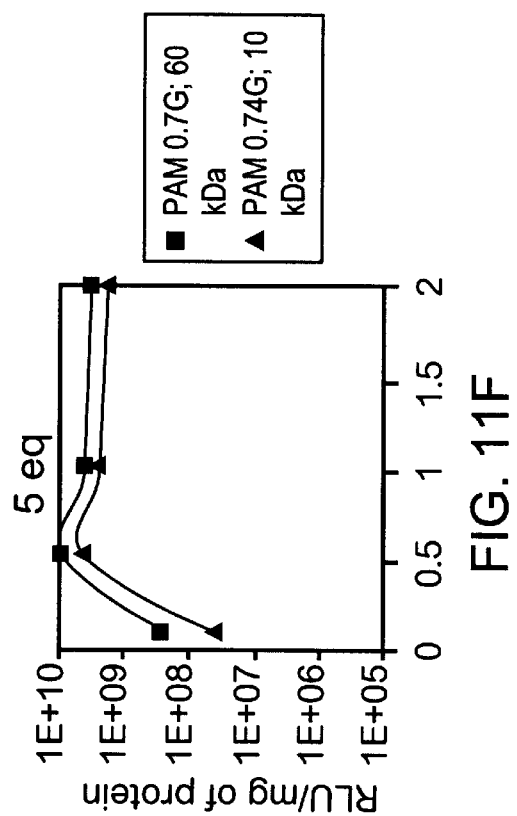
Figure 11E:
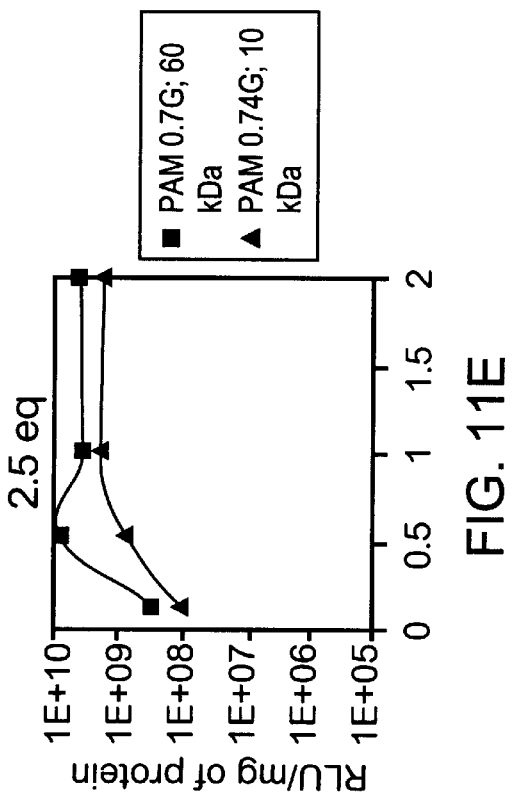

FIG. 10: Influence of the level of substitution of the cationic polymer on the transfection efficiency. The black columns indicate that the experiment was conducted in the presence of chloroquine, the white columns in the absence of chloroquine.

FIG. 11: Influence of the size of the polymers on the transfection efficiency, in the presence or in the absence of chloroquine. Cq: chloroquine. The curves identified by ● present the results observed with PAM 0.7G, 60 kDa and the curves identified by ▲ present the results observed with PAM 0.74G, 10 kDa.

FIG. 12: Gene transfer into Hela cells. The complexes used contain PAM 0.7G at different charge equivalents (1.5, 2.5 or 5 Eq) indicated on the x-axis. The light columns represent the results observed in the absence of chloroquine, the dark columns represent the results observed in the presence of chloroquine.

Figure 13:
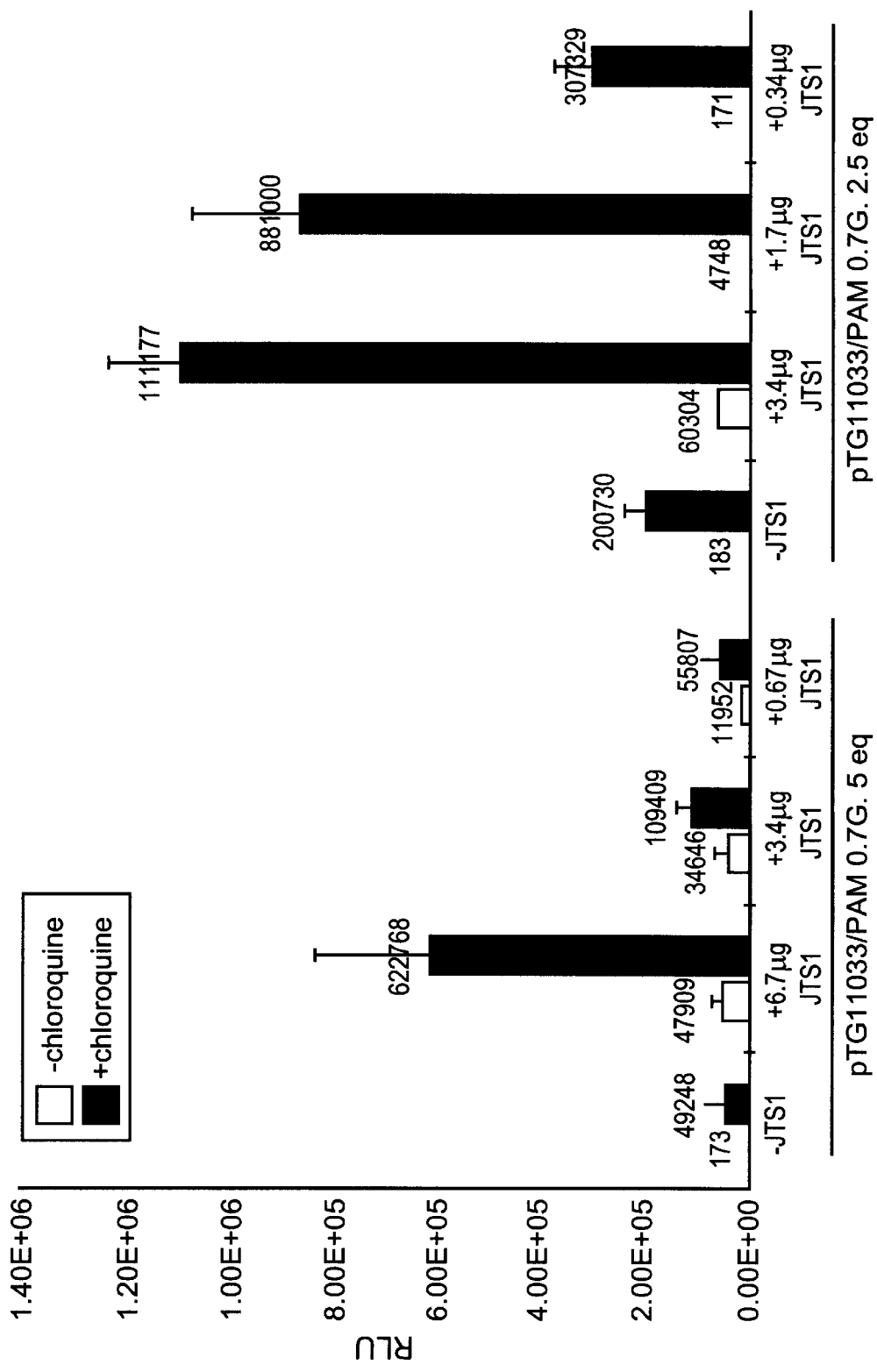

FIG. 13: Effect of the addition of JTS-1 to the PAM 0.7G complexes on the transfection of A549 cells. The quantities of peptide JTS-1 added are indicated on the x-axis. The white columns represent the results observed in the absence of chloroquine and the black columns in the presence of chloroquine. The luciferase activity is expressed in RLU measured over 15 seconds.

Figure 14:
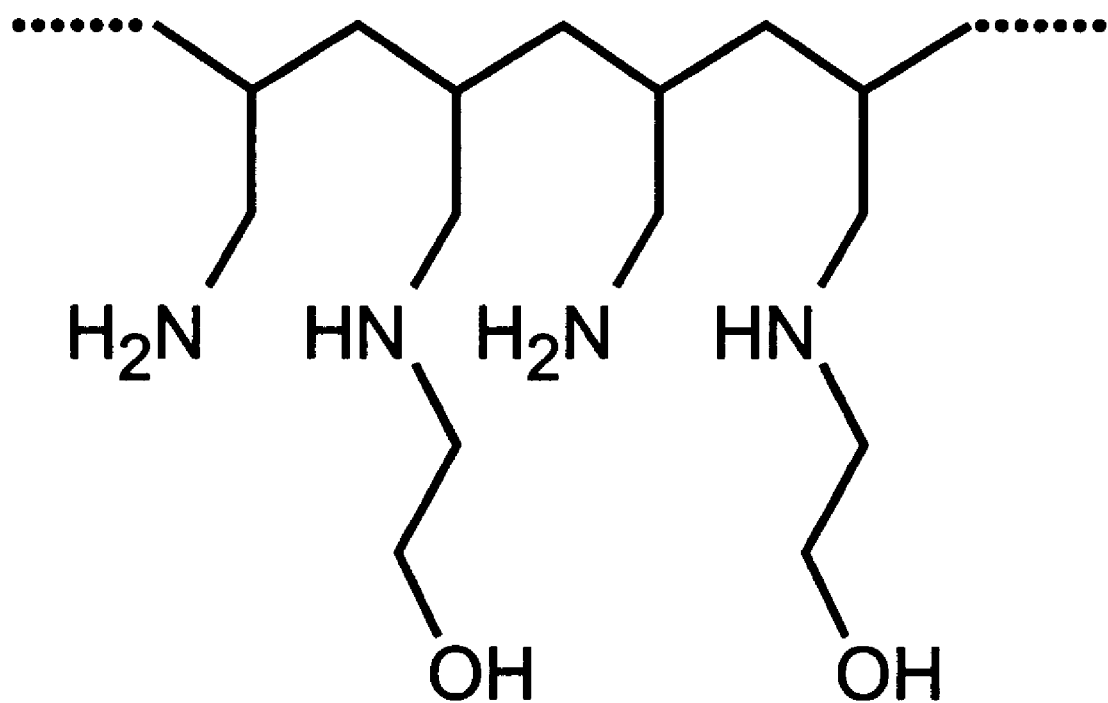

FIG. 14: Structure of the ethoxylated polyallylamine.

Figure 15:
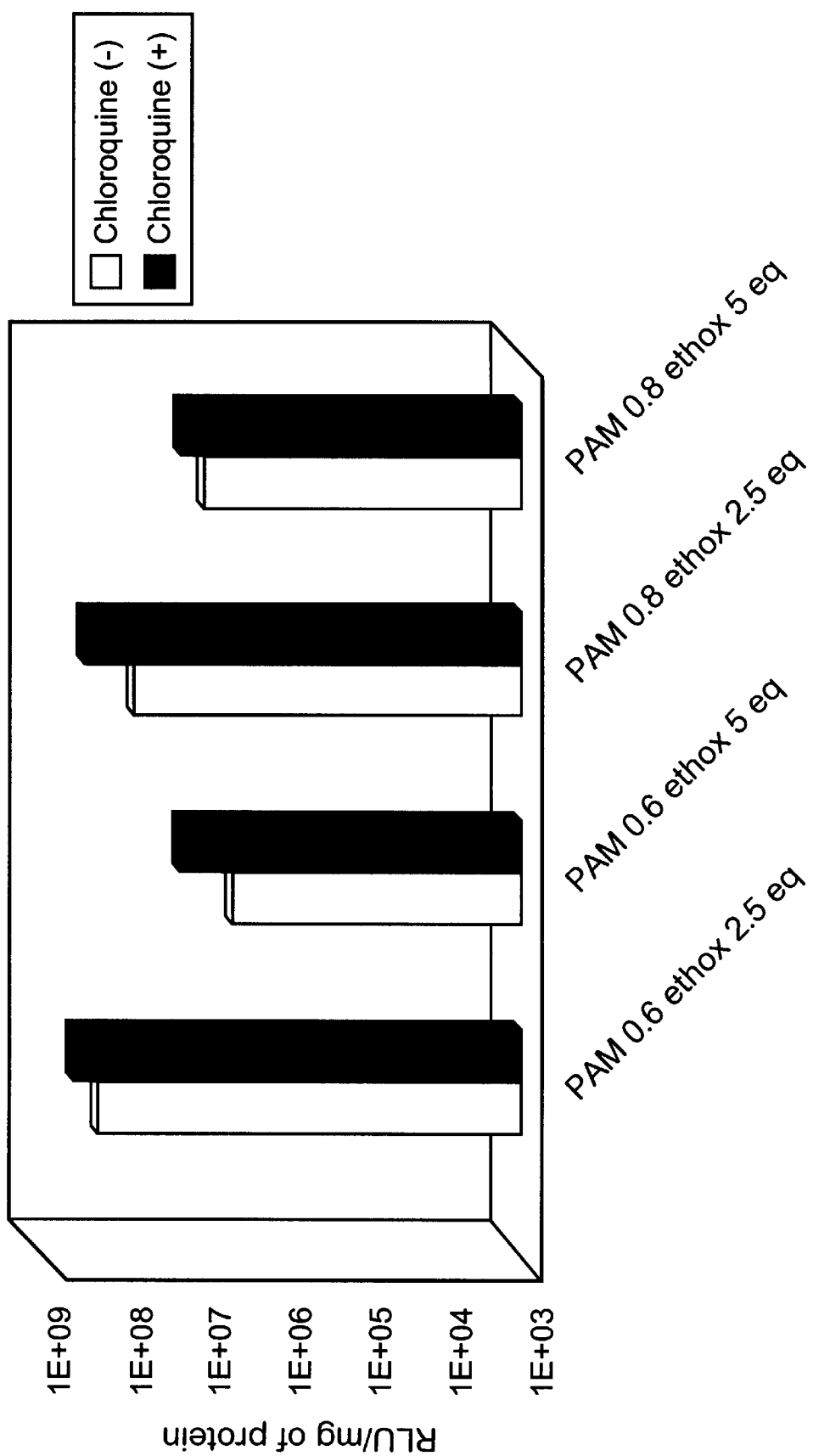

FIG. 15: Transfection of the A549 cells with the ethoxylated PAMs: PAM/0.6E or PAM/0.8E. The white columns represent the results observed in the absence of chloroquine and the black columns in the presence of chloroquine. The charge equivalents analyzed are indicated on the x-axis.

Figure 16:
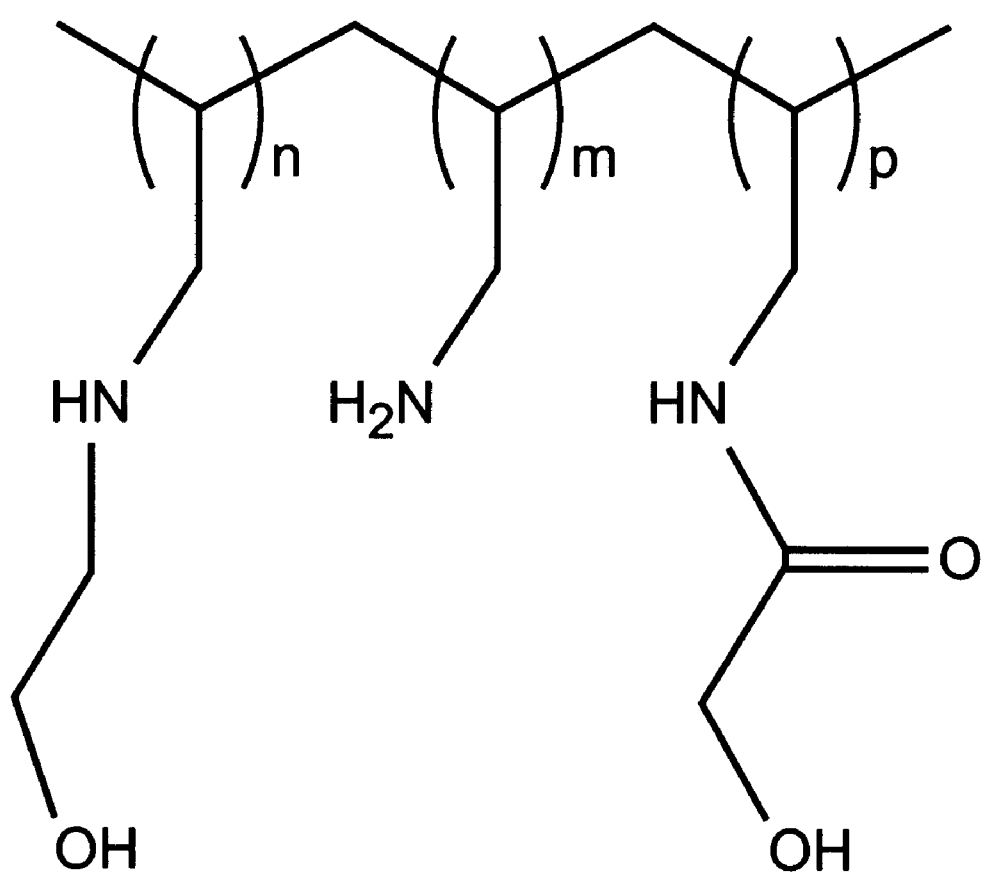

FIG. 16: Structure of the glycolylated/ethoxylated polyallylamine.

Figure 17:
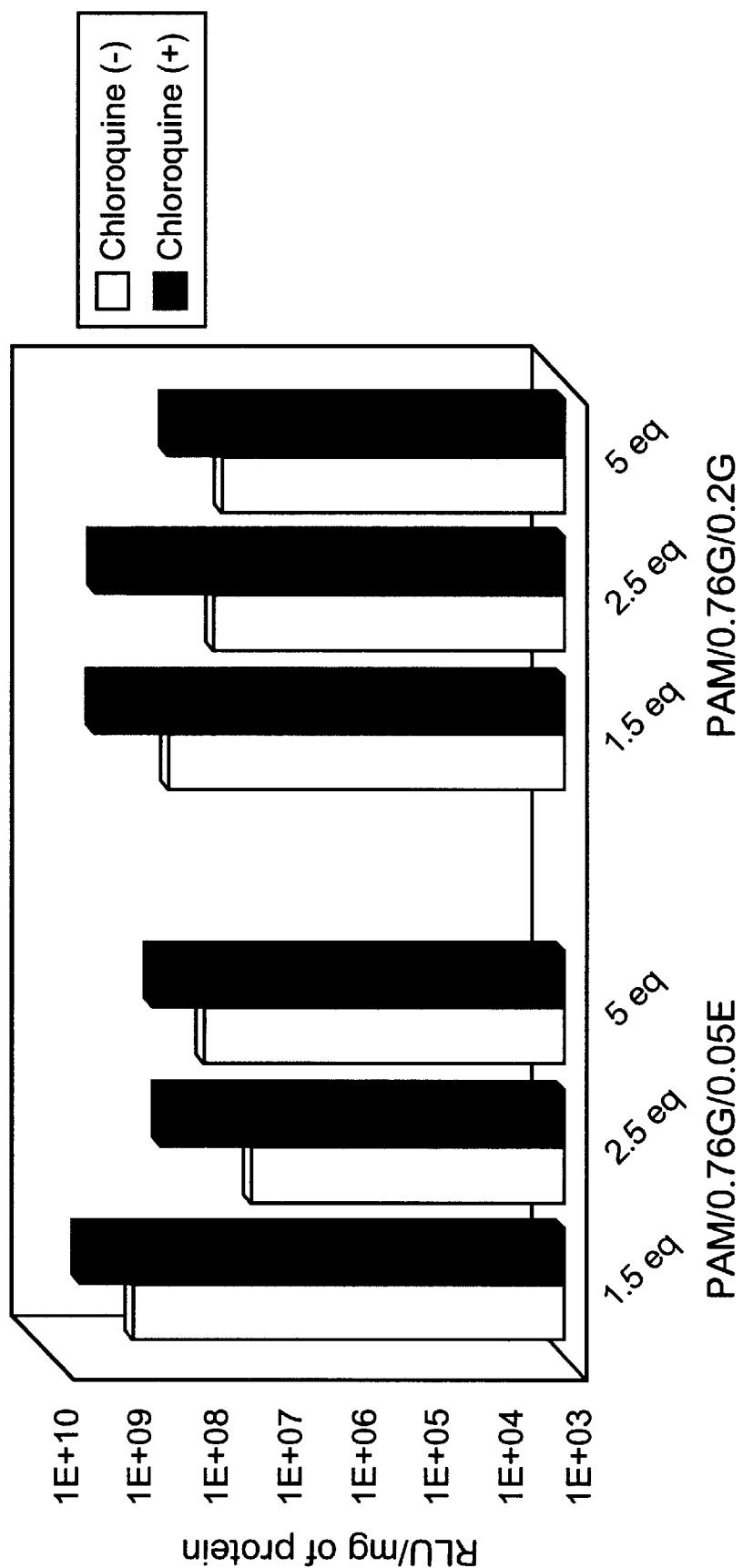

FIG. 17: Transfection of A549 cells with the 76% glycolylated/5 or 20% ethoxylated PAMS. The white columns represent the results observed in the absence of chloroquine and the black columns in the presence of chloroquine. The charge equivalents analyzed are indicated on the x-axis.

Figure 18:
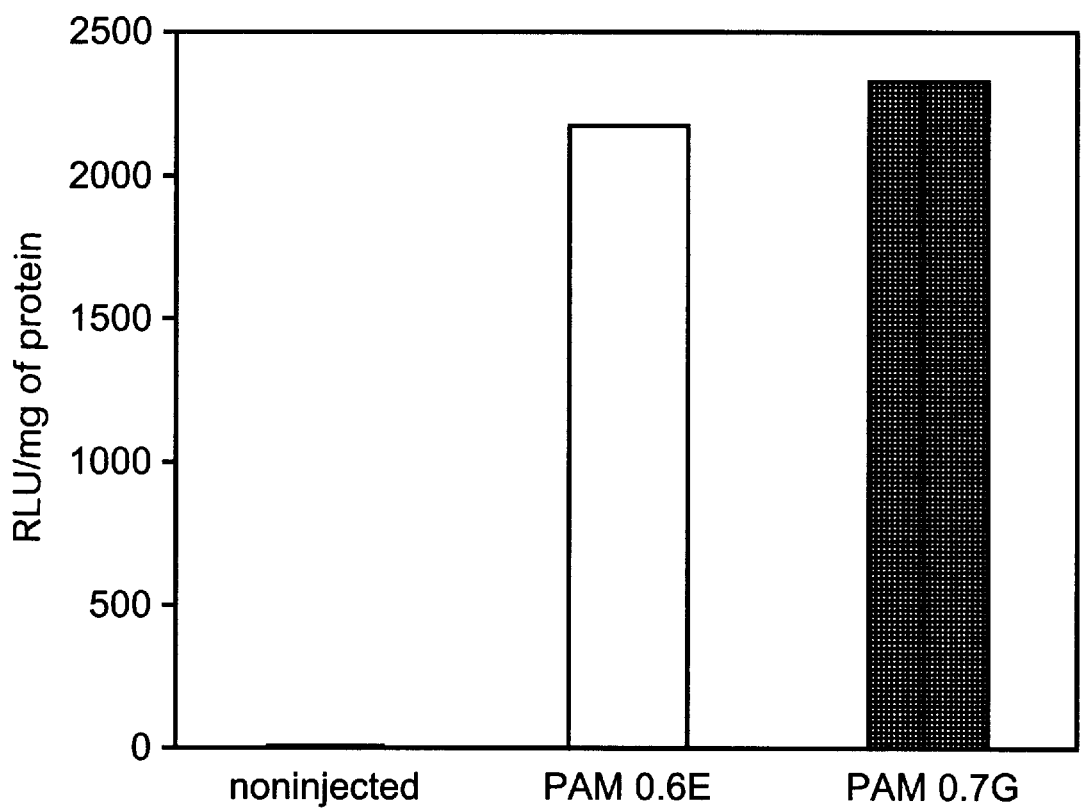

FIG. 18: Intravenous injection of PAM/0.7G or PAM/0.GE into mice at a fixed charge level of 5.

EXAMPLES

A—MATERIALS AND METHODS

1. Chemical Synthesis of the Glycolilated Polyallylamines (FIG. 1)

280 mg of polyallylamine, HCl (PAM, p=592; 55 kDa; that is to say 3 mmol of ammonium function) [Aldrich] are dissolved at 67° C. for about 10 min in 1 ml of double distilled water. The solution is then placed at room temperature. 230 µl of methyl glycolate (Fluka) (3 mmol) and 500 µl triethylamine (TEA) (Fluka) are added sequentially and stirred at room temperature for 72 h. After evaporating the water under reduced pressure, the solid mass is taken up in a 50/50 double distilled water/36% ammonium hydroxide mixture, and then subjected to another evaporation. This treatment is carried out twice in order to completely eliminate the TEA. The solid finally obtained is taken up in (5 ml) double distilled water, acidified to pH 1 (HCl), and then precipitated by addition of 500 ml of acetone. The precipitate is recovered by filtration and dried under vacuum for 12 h. The polymer is dissolved in (5 ml) double distilled water and then lyophilized. The product thus obtained is substituted at 50% (PAM/0.5G).

The synthesis of PAM substituted at 70% (PAM/0.7G) or of polylysine glycolilated at 70% (PLL/0.7G) is carried out according to a variant of this protocol for which 6 mmol of methyl glycolate are added.

The level of substitution of the different products is determined by proton NMR.

2. The Cells

The cells A549 (pulmonary carcinoma) and MRC5 (pulmonary fibroblasts) are respectively maintained in culture in a DMEM medium (Dulbecco's modified medium) or MEM medium (minimum essential medium) supplemented with 10% fetal calf serum, 286 mg/ml of glutamine and 2 g/l of glucose, in an incubator at 37° C., in an atmosphere saturated with moisture containing 5% $CO_2$. At confluence, the cells are detached from the support by treatment with trypsin-EDTA and reinoculated into a culture flask containing 15 ml of fresh medium. About 18 hours before the transfection step, the cell cultures are distributed into multiwell plates, in medium containing 10% fetal calf serum so as to obtain 70–80% confluence during the transfection.

3. The Plasmid

The polynucleotide chosen, the plasmid pTG11033 (FIG. 2), contains the gene encoding luciferase placed under the control of the CMV promoter, the HMG gene intron 1 and the SV40 polyA termination signal.

4. Preparation of the Various Solutions of PAM/0.5G and PAM/0.7G Polymers

The concentrations of the solutions prepared are expressed in millimole of unsubstituted $NH_2$ monomer for a given polymer. 10 mM $NH_2$ solutions are prepared and stored at 4° C.

PAM/0.5G 10 mM ($NH_2$): Molecular Weight 50860.4

One mole of PAM/0.5G corresponds to 295.7 moles of unsubstituted $NH_2$ amine functions. 45.5 mg of PAM/0.5G (0.9 µmol and therefore 264 µmol of $NH_2$) are dissolved in 26.4 ml of double distilled water so as to obtain a 10 mM ($NH_2$) solution.

PAM/0.7G 10 mM ($NH_2$): Molecular Weight 57720.6

One mole of PAM/0.7G corresponds to 177.4 moles of unsubstituted $NH_2$ amine functions. To obtain a 10 mM ($NH_2$) solution, 58 mg of PAM/0.5G (0.9 µmol and therefore 160 µmol of $NH_2$) are dissolved in 16 ml of double distilled water.

5. Preparation of the DNA/polymer (PAM/0.5G or PAM/0.7G) Complexes

In two 1.5 ml Eppendorf tubes, the required (see table below) quantities of polymer and of plasmid are respectively diluted in 150 µl of NaCl or 150 µl of 20 mM HEPES, pH 7.5. The solution is mixed on a vortex and then centrifuged. After 10 min, the two solutions. are mixed and the mixture is placed at room temperature. After incubating for 10 min, the complexes formed may be used for the transfection of cells.

| number of equivalents (eq.) | 2.5 | 5 |
| --- | --- | --- |
| Volume of solution of polymer 10 mM ($NH_2$) | 1.5 µl/2 µg*<br>3 µl/4 µg* | 3 µl/2 µg*<br>6 µl/4 µg* |

*Quantity of plasmid.

The proportion of protonated amines of the polymer at a given pH not being known exactly, the complexes analyzed are expressed as equivalents (eq) of nitrogen relative to the phosphate of the DNA (N/P). Thus, one equivalent will represent the quantity of polymer required to have one nitrogen per phosphate group of the DNA (Felgner et al., 1997, Human Gene Therapy, 8. 511–512).

6. Transfection

100 µl of the complex obtained at point 5 are poured over the cells distributed into multiwells as described above, previously rinsed with serum-free fresh medium. After 2 to 3 h, the medium is replaced by medium supplemented with 10% fetal calf serum. The level of expression of the luciferase gene is measured after 48 h. For that, the transfected cells are lysed in a lysis buffer (Promega). The cellular debris is then removed by centrifugation and the luciferase activity (in RLU/min, relative light unit per minute) is measured on 20 μl of supernatant in accordance with the supplier's (Promega) instructions by adding 100 μl of reagent and measuring the activity by luminescence. The quantity of total protein is moreover determined by the calorimetric method of bicinchoninic acid BCA (Smith et al., 1985, Anal. Biochem., 150, 76–85 Pierce) using an aliquot of supernatant. This makes it possible to express the luciferase activity in RLU per milligram of protein extracted from the cells.

7. Transfection in the Presence of 100 μM Chloroquine:

According to a variant of the transfection technique provided above, the required volume of a 10 mM solution of chloroquine is added to the culture medium just before the addition of the DNA/polymer complex so as to obtain a final concentration per well of 100 μM.

B—RESULTS

Example 1

Gene Transfer into the A549 Cells and Influence of the Charge of the DNA/cationic Polymer Complex In a first instance, various complexes are formed according to the protocol disclosed above by adding two different quantities of PAM/0.5G 10 mM or of PAM/0.7G 10 mM to a fixed quantity of plasmid (2 μg), so as to obtain different N/P ratios (equivalents: 2.5 or 5 eq). This makes it possible to study if the total charge of the complex formed by electrostatic interactions between the amines of the cationic polymer analyzed and the phosphates of the plasmid DNA plays a role in the transfection efficiency. The results (FIG. 3) show that the PAMs glycolilated at 50% or at 70% are capable of efficiently transferring the DNA into the cells, even at low charge equivalent. It may be noted, moreover, that the presence of chloroquine (100 μM) makes it possible to enhance the transfection efficiency.

Example 2

Effect of the Quantity of DNA on the Transfection Efficiency

The complexes for this series of experiments are formed by mixing increasing quantities of plasmid DNA (2, 4 or 6 μg) and variable quantities of PAM/0.5G or of PAM/0.7G so as to obtain N/P ratios of 1.5 eq, 2.5 eq or 5 eq. The results obtained (FIG. 4) after transfection of the A549 cells with these different complexes show that the PAM/0.5G and PAM/0.7G polymers allow efficient transfection of the cells, with or without chloroquine, regardless of the quantity of DNA. It is in addition important to note that chloroquine is not essential for obtaining a high efficiency level when a DNA/PAM/0.7G complex prepared from 4 μg of DNA and from 5 charge equivalents is used for the transfection.

Example 3

Transfer of Genes into the MRC5 Cells

It is known that the efficiency of the gene transfer using nonviral vectors can vary in particular according to the cell type considered. We therefore tested our transfection system on another tumor cell type, the MRC5s, which are considered as cells which are difficult to transfect (Boussif et al., 1996, Gene Therapy, 3, 1010–1017). The complexes were prepared as described above by mixing variable quantities of plasmid DNA (2 or 4 μg) and variable quantities of cationic polymers PAM/0.5G or PAM/0.7G so as to obtain charge equivalent values of 2.5 or 5 eq. Moreover, the transfections were carried out in the presence or in the absence of chloroquine (100 μM).

The results presented in FIG. 5 show that the MRC5 cells are efficiently transfected under the experimental conditions tested.

Example 4

Comparison of the Transfection Efficiencies for PAM/0.7G and PLL/0.7G

In order to show the importance of the chemical nature of the polymer, the transfection efficiencies for PAM/0.7G to those observed with an analog obtained from polylysine (PLL) in which 70% of the free $NH_2$ functions have been glycolilated as described in A.1. (FIG. 6).

The transfection of the A549 cells was carried out as described above using DNA/cationic polymer complexes for which said polymer is PAM/0.7G or PLL/0.7G or unsubstituted polylysine. In addition, these complexes were prepared with different quantities of DNA (2 or 4 μg), and by varying the N/P ratio (2.5 or 5 eq).

The results obtained (FIG. 7) show that the substitution of the PLL polymer at 70% does not make it possible to improve the low levels of expression observed with the unmodified polylysine (PLL) which are 50 to 100 times lower than those observed under identical conditions with PAM/0.7G.

Example 5

Cytotoxicity of the Polymers and of the DNA/ polymer Complexes

The cytotoxicity of the substituted or unsubstituted PAM polymers was analyzed by carrying out a calorimetric test with MTT (3-(4,5-dimethylthioazol-2-yl)-2,5-diphenyltetrazolium bromide) (Mossman T., 1983, Journal of Immunological Methods, 65, 55–63).

In a first instance, the A549 cells in culture are placed in the presence of increasing quantities of noncomplexed polymers. These quantities correspond to the quantities necessary to form complexes with 4 μg of DNA and to obtain N/P ratios ranging from 2.5 to 30 eq.

The results (FIG. 8) show that PAM/0.5G and PAM/0.7G are a lot less toxic to cells than the unsubstituted PAM polymer (remark: 100% viability corresponds to the cells which have not been subjected to any treatment).

In a second instance, a series of similar experiments was carried out with the same polymers in a cationic polymer/ DNA (4 μg of plasmid) complex form. The levels of cell viability presented in FIG. 9 confirm that the cationic polymer/DNA complexes according to the invention have a very low toxicity toward the cells.

The cell viability observed with PAM/0.7G at 30 equivalents is greater than 70%. This is very promising for the trials in vivo for which the quantities of DNA and consequently of polymer to be used may be substantial.

Example 6

Gene Transfer into A549 cells and Influence of the Level of Substitution of the Cationic Polymer Various cationic polymers according to the invention are prepared whose level of substitution varies from 70 to 85%.

In accordance with the protocols set out above, several complexes are formed starting with a fixed quantity of plasmid pTG11033 (2 µg) and with these various cationic polymers (0.7G, 0.74G, 0.76G, 0.79G, 0.85G) so as to obtain different N/P ratios (equivalents: 1.5, 2,5 or 5 eq). This makes it possible to study if the level of substitution of the polymer plays a role in the transfection efficiency. For each series, five independent experiments were carried out. Moreover, the polymer ExGen500 (Euromedex, Souffelweirsheim, France) complexed with 2 µg of plasmid is used as standard. The results (FIG. 10) show that the PAMs glycolilated from 70% to about 76% are capable of efficiently transferring the DNA into the cells, even at a low charge equivalent, and that above (79 and 85%), a decrease in efficiency is observed, with or without chloroquine (100 µM).

Example 7

Effect of the Size of the Polymers

Cationic polymers according to the invention, with two different degrees of polymerization (60 kDa and 10 kDa Aldrich) exhibiting comparable levels of substitution (74% and 70%) are prepared. Complexes are formed according to the protocols described above for which the quantity of plasmid complexed varies from 0.1 to 2 µg, the N/P ratios vary from 1.5, 2.5 to 5 eq. The results obtained (FIG. 11) after transfection of the A549 cells with these different complexes, in the presence or in the absence of chloroquine, show that the size of the polymer used does not influence its capacity to transfect the cells.

Example 8

Gene Transfer into HeLa Cells

We also tested our transfection system on another cell type, the HeLa cells, a line derived from a human cervical carcinoma. The complexes were prepared as described above by mixing 2 µg of plasmid DNA and variable quantities of cationic polymers PAM/0.7G so as to obtain values of charge equivalents from 1.5, 2.5 or 5 eq. Moreover, the transfections were carried out in the presence or in the absence of chloroquine (100 µM). The results presented in FIG. 12 show that the HeLa cells are efficiently transfected under the experimental conditions tested.

Example 9

Influence of an Endosome-disrupting Peptide on the Transfection Efficiency

In this example, we carried out experiments for the transfection of the complexes pTG11033/PAM0.7G, 2.5 eq or pTG11033/PAM 0.7G, 5 eq in combination with an endosome-disrupting peptide (peptide JTS1 described by Gottschalk et al., 1996, Gene Therapy, 3, 448–457).

About 24 hours before the transfection, "24-well" plates are inoculated with $10^5$ A549 cells per 1-ml well. The culture medium is DMEM+glutamine+gentamycin+10% fetal calf serum. The next day, different quantities of JTS1 (see FIG. 13) are added to 20 µl of complexes pTG11033/PAM 0.7G, 5 eq or pTG11033/PAM 0.7G, 2.5 eq (these complexes are prepared as described above and contain 2 µg of pTG11033). After incubating for 30 minutes at room temperature, the mixtures are diluted in serum-free DMEM medium so as to obtain a final plasmid concentration of 1 µg/ml. 200 µl of this preparation (that is to say the equivalent of 200 ng of plasmid) are deposited on the cells (for each of the complexes, the experiment is reproduced on 3 different wells) in the absence or in the presence of chloroquine (100 µM final) after aspiration of the culture medium. 800 µl of medium containing 10% of serum are added 3 to 4 hours after the transfection.

The expression of the gene encoding luciferase is measured 24 hours after the transfection. The transfected cells are lysed in 100 µl of lysis buffer (Promega) and frozen at −80° C. After thawing, 20 µl of extracts are removed for assaying the luciferase. A Microlumat luminometer (Berthold Microlumat LB96P) is used to quantify the production of luciferase. 100 µl of reagent (Luciferase assay system, Promega) are added to the extracts and the luminescence expressed in RLU is measured over 15 sec.

The results (FIG. 13) show that the addition of JTS1 makes it possible to increase the transfection efficiency by about 250 to 300 fold in the absence of chloroquine. In the presence of chloroquine, the efficiency of transfection of the PAM 0.7G complexes is substantially increased. The addition of JTS1 makes it possible to increase the transfection efficiency by 5 (PAM 0.7G, 2.5 eq) to 13 fold (PAM 0.7G, 5 eq).

Example 10

Chemical Synthesis of the Ethoxylated Polyallylamines PAM/0.6E and PAM/0.8E (FIG. 14)

In accordance with the present invention, we prepared polyallylamines substituted with another hydrophilic group. To do this, 0.2854 g (2.762 mmol of amine function) of PAM-HCl (Aldrich-28, 322–3) dissolved in 0.5 ml of millipore-treated water are added to 198 ml of iodoethanol (0.92 equivalents—2.541 mmol) There are then added a) 2 ml of DMSO so as to satisfy the iodoethanol solubility constraints and b) 0.74 ml of triethylamine (5.524 mmol). After stirring at 30° C. for 72h00, the medium is evaporated under vacuum, and three coevaporations with 18% ammonium hydroxide make it possible to eliminate the triethylamine. The residue is taken up in water and is then acidified by addition of concentrated HCl. The final volume of the aqueous phase is 60 ml. Three extractions with 20 ml of ether are carried out in order to eliminate most of the residual iodoethanol. The aqueous phase is concentrated in a Rotavap™ and then precipitated in 600 ml of acetone. After filtration on sintered glass, the solid is taken up in water. After dialysis against several baths with 4 l of millopore-treated water, the sample is lyophilized. The degree of functionalization is determined by proton NMR. According to the conditions described above, 60% of the primary amine functions of the polymer are ethoxylated. In an identical manner, the protocol is adapted so as to obtain polymers in which 80% of the primary amine functions are ethoxylated.

Example 11

Transfection of the A549 Cells with the Ethoxylated PAMs: PAM/0.6E or PAM/0.8E

The DNA/polymer (PAM/0.6E or PAM/0.8E) complexes are prepared under the same conditions as those described above for the preparation of the complexes comprising glycolylated PAMs, in particular the charge equivalents are defined in the same manner (amine potentially protonable/phosphate of the DNA). In accordance with the protocol described for the glycolylated PAMs, the A549 cells are transfected with 2 μg of plasmid pTG11033 complexed with the desired quantity of polymer, in the presence or in the absence of chloroquine (100 μM final). The luciferase activity is measured after 48 hours of incubation. The results (FIG. 15) confirm that the substitution of the polyallylamines with a group of a hydrophilic nature makes it possible to observe an efficient transfection level, in the presence and in the absence of chloroquine.

Example 12

Transfection of the A549 Cells with both Ethoxylated and Glycolylated PAMs: PAM/0.706G/0.05E or PAM/0.76G/0.2E The DNA/polymer (PAM/0.76G/0.05E or PAM/0.76G/0.2E) complexes are prepared under the same conditions as those described above for the preparation of the complexes comprising glycolylated PAMs, in particular the charge equivalents are defined in the same manner (amine potentially protonable/phosphate of the DNA). In accordance with the protocol described for the glycolylated PAMs, the A549 cells are transfected with 2 μg of plasmid pTG11033 complexed with the desired quantity of polymer, in the presence or in the absence of chloroquine (100 μM final). The luciferase activity is measured after 48 hours of incubation. The results (FIG. 17) confirm that the substitution of the polyallylamines with a group of a hydrophilic nature makes it possible to observe an efficient transfection level, in the presence and in the absence of chloroquine.

Example 13

Intravenous Injection of Glycolylated PAM: PAM/0.7G or of Ethoxylated PAM: PAM/0.6E into Mice The results are presented in FIG. 18. DNA/polymer complexes according to the invention were synthesized in a 5% glucose solution according to the methods described above starting with the cationic polymer PAM 0.7G or the cationic polymer PAM 0.6E, at a fixed charge ratio of 5, using a plasmid containing the luciferase gene pTG11033 (French patent application No. 97/08267).

The mice used are 6-week old female C57BL/6 mice. The intravenous injections are carried out into the tail after disinfecting the skin with 70% ethanol. The injected volume is 250 μl and the DNA concentration is 0.24 mg/ml. A day after the injections, the mice are sacrificed. After extraction, the tissues are frozen in liquid nitrogen. In order to measure the luciferase activity, the tissues are placed in 200 or 500 μl of lysis buffer (Promega) and then ground with the aid of a Polytron homogenizer (Kinenatica). The tissues are subjected to a homogenization of 2×30 s and for the first 5 s, the speed of rotation of the polytron is gradually increased up to the maximum (position 11 on the apparatus). The homogenate thus obtained from lungs is subjected to three freeze/thaw steps. The cellular debris is pelleted by centrifugation and the luciferase activity (in RLU/min, relative light unit per minute) is measured on 20 μl of supernatant in accordance with the supplier's (Promega) instructions by adding 100 μl of reagent and by measuring the activity by luminescence (Berthold luminometer 9500). The quantity of total protein is, moreover, determined by the calorimetric method of bicinchoninic acid BCA (Smith et al., 1985, Anal. Biochem., 150, 76–85 Pierce) starting with an aliquot of supernatant. This makes it possible to express the luciferase activity in RLU per milligram of proteins extracted from the tissues. Noninjected mice were used as negative control. The results show expression of the luciferase reporter gene in the lungs after intravenous injection of complexes as described above compared with the noninjected mice. The values indicated are the mean values obtained starting with 2 (noninjected), 3 (PAM 0.7G) and 1 (PAM 0.6 E) injected mice.

What is claimed is:

1. A complex comprising (i) at least one cationic regular polymer of formula I:

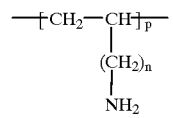

in which n is a whole number varying from 0 to 5 and p is a whole number varying from 2 to 20,000, wherein at least 10% of the free $NH_2$ functions are substituted with identical or different hydrophilic R groups; and (ii) at least one nucleic acid or protein comprising at least one negative charge.

2. The complex according to claim 1, wherein said cationic regular polymer has the formula:

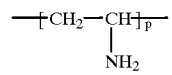

(n=0).

3. The complex according to claim 1, wherein said cationic regular polymer has the formula:

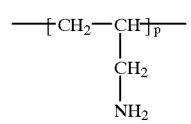

(n=1).

4. The complex according to claim 1, wherein said hydrophilic R groups of said cationic regular polymer comprise at least one function selected from the group consisting of amine, hydroxyl, amide and ester functions.

5. The complex according to claim 1, wherein R is chosen from the groups R'—C=O and —$(CH_2)_{n'}$—R' where R' is a group containing at least one hydrophilic function and n' is 1 to 5.

6. The complex according to claim 1, where R or R' is a polymer exhibiting hydrophilic properties.

7. The complex according to claim 6, wherein R or R' is selected from the group consisting of polyethylene glycol and its derivatives, polyvinylpyrrolidone, polymethyloxazoline, polyhydroxypropyl methacrylamide, polylactic acid, polyglycolic acid and cellulose derivatives.

8. The complex according to claim 7, wherein R or R' is polyethylene glycol (PEG) having a molecular weight varying from 300 to 5000.

9. The complex according to claim 3, wherein said cationic regular polymer (i) is a glycolilated polyallylamine.

10. The complex according to claim 9, wherein about 50 to about 70% of free $NH_2$ functions of said polymer are substituted with R, and wherein R is

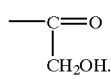

11. The complex according to claim 3, wherein said cationic regular polymer (i) is an ethoxylated polyallylamine.

12. The complex according to claim 11, wherein about 50 to about 80% of free $NH_2$ functions of said regular polymer are substituted with R, and R is —$(CH_2)_2$—OH.

13. The complex according to claim 10, wherein p in said regular polymer (i) is 592.

14. The complex according to claim 1 wherein said targeting element is present in said cationic regular polymer and it is selected from the group consisting of the whole or part of sugars, peptides, oligonucleotides, lipids, hormones, vitamins, antigens, antibodies, ligands, fusogenic peptides, nuclear localization peptides, or a combination of such compounds.

15. The complex according to claim 1, wherein the active substance is chosen from nucleic acids and proteins.

16. The complex according to claim 15, wherein said active substance is a cDNA, a genomic DNA, a plasmid DNA, a messenger RNA, an antisense RNA, a ribozyme, a transfer RNA, a ribosomal RNA, or a DNA encoding said RNAs.

17. The complex according to claim 16 wherein said nucleic acid comprises a gene and elements for expressing said gene.

18. The complex according to claim 17, wherein said gene encodes the whole or part of a ribozyme, an antisense nucleic acid, a polypeptide, or is a marker.

19. The complex according to claim 1, wherein the ratio between the number of positive charges of said cationic regular polymer (i) and the number of negative charges of said active substance (ii) varies from 1 to 30.

20. A method of preparing a complex according to claim 1, wherein one or more cationic regular polymers of formula:

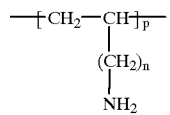

in which n is a whole number varying from 0 to 5 and p is a whole number varying from 2 to 20,000:
at least 10%, of the free $NH_2$ functions are substituted with identical or difference hydrophilic R groups;
said cationic regular polymer may in addition comprise at least one targeting element combined covalently or not with the free $NH_2$ functions and/or with said hydrophilic R groups provided that said cationic regular polymer contains at least 20%, of free $NH_2$ functions, are brought into contact with one or more active substances comprising at least one negative charge and in that said complex is recovered optionally after a purification step.

21. A composition, comprising at least one complex according to claim 1 and a pharmaceutically acceptable carrier.

22. The composition according to claim 21, further comprising at least one adjuvant which enhances the transfection of said complex into a target cell in vitro, ex vivo or in vivo.

23. The composition according to claim 22, wherein said adjuvant comprises a lysosomotropic agent a protic polar compound selected from the group consisting of propylene glycol, polyethylene glycol, glycerol, ethanol, 1-methyl-L-2-pyrrolidone and derivatives thereof, or an aprotic polar compound selected from the group consisting of dimethyl sulfoxide (DMSO), diethyl sulfoxide, di-n-propyl sulfone sulfolane, dimethylformamide, dimethylacetamide, tetramethylurea, acetonitrile and derivatives thereof.

24. Cationic regular polymer of formula I:

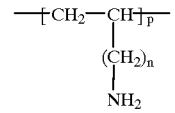

in which n is a whole number varying from 0 to 5 and p is a whole number varying from 2 to 20,000, wherein
at least 10% of the free $NH_2$ functions are substituted with identical or different hydrophilic R groups selected from the group consisting of polymethyloxazoline, polyethyloxazoline, polyglycolic acid or cellulose derivatives,
said cationic regular polymer may in addition comprise at least one targeting element combined covalently or not with the free $NH_2$ functions and/or with said hydrophilic R groups provided that said cationic regular polymer contains at least 20%, of free $NH_2$ functions.

25. The regular polymer according to claim 24, wherein R is selected from the group consisting of 5'—C=O and —$(CH_2)_{n'}$—R' where R' is a group containing at least one hydrophilic function, and n' is 1 to 5.

26. The regular polymer according to claim 25, wherein R' is selected from the group consisting of polymethyloxazoline, polyethyloxazoline, polyglycolic acid and cellulose derivatives.

27. The regular polymer according to claim 24, wherein said regular polymer is a glycolilated polyallylamine.

28. The regular polymer according to claim 27, wherein R is

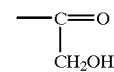

and about 50 to about 70% of free $NH_2$ functions are substituted with R.

29. The regular polymer according to claim 24 wherein said regular polymer is an ethoxylated polyallylamine.

30. The regular polymer according to claim 29, wherein that R is $(CH_2)_2$—OH
and about 50 to about 80% of free $NH_2$ functions are substituted with R.

31. The regular polymer according to claim 28, wherein p=592.

32. The regular polymer according to claim 24, wherein said targeting element is present and is selected from the group consisting of the whole or part of sugars, peptides, oligonucleotides, lipids, hormones, vitamins, antigens, antibodies, ligands, fusogenic peptides, nuclear localization peptides and a combination of such compounds.

33. The complex of claim 1, wherein said cationic regular polymer further comprises at least one targeting element combined covalently or non-covalently with the free $NH_2$ functions and/or with said hydrophilic R groups provided that said cationic regular polymer contains at least 20% of free $NH_2$ functions.

* * * * *